US012329564B2

(12) United States Patent
Lee et al.

(10) Patent No.: US 12,329,564 B2
(45) Date of Patent: Jun. 17, 2025

(54) ELECTRONIC DEVICE FOR AUSCULTATION AND METHOD OF OPERATION THEREOF

(71) Applicant: SMARTSOUND CORPORATION, Seoul (KR)

(72) Inventors: Manchan Lee, Seoul (KR); Jungho Lee, Seoul (KR)

(73) Assignee: SMARTSOUND CORPORATION, Seoul (KR)

( * ) Notice: Subject to any disclaimer, the term of this patent is extended or adjusted under 35 U.S.C. 154(b) by 0 days.

(21) Appl. No.: 18/634,625

(22) Filed: Apr. 12, 2024

(65) Prior Publication Data
US 2024/0341716 A1 Oct. 17, 2024

(30) Foreign Application Priority Data

Apr. 13, 2023 (KR) .......................... 10-2023-0048824

(51) Int. Cl.
*A61B 7/04* (2006.01)
*A61B 5/00* (2006.01)
(Continued)

(52) U.S. Cl.
CPC ............ *A61B 7/04* (2013.01); *A61B 5/02055* (2013.01); *A61B 5/7267* (2013.01);
(Continued)

(58) Field of Classification Search
USPC ................................................. 600/300–301
See application file for complete search history.

(56) References Cited

U.S. PATENT DOCUMENTS 6,244,376 B1 * 6/2001 Granzotto ................ A61B 7/02
181/131
6,491,647 B1 * 12/2002 Bridger ................ G01L 1/2231
128/900
(Continued)

FOREIGN PATENT DOCUMENTS

JP 2021-133005 A 9/2021
JP 2022-530855 A 7/2022
(Continued)

OTHER PUBLICATIONS

Search Report dated Jan. 8, 2024 issued in International Application No. PCT/KR2023/012042.
(Continued)

*Primary Examiner* — Allen Porter
*Assistant Examiner* — Michael T. Holtzclaw
(74) *Attorney, Agent, or Firm* — Nath, Goldberg & Meyer; Joshua B. Goldberg

(57) ABSTRACT

An electronic device includes a housing with a handle formed on one part of the housing, a display, a sound collecting part, and a controller. A handle is formed on one part of the housing and the display is positioned on another part of the housing and placed on one surface side of the housing. The sound collecting part is positioned on the housing on another surface side of the housing. The controller is configured to input first auscultation sound data obtained through the sound collecting part into a first AI model. The device obtains an abnormality analysis result corresponding to the first auscultation sound data and provides the abnormality analysis result through the display.

17 Claims, 17 Drawing Sheets

(51) Int. Cl.
*A61B 5/0205* (2006.01)
*A61B 7/00* (2006.01)

(52) U.S. Cl.
CPC ............ *A61B 5/7282* (2013.01); *A61B 5/742* (2013.01); *A61B 5/0077* (2013.01); *A61B 7/003* (2013.01); *A61B 2560/0431* (2013.01)

(56) References Cited

U.S. PATENT DOCUMENTS

| | | | |
|---|---|---|---|
| 10,709,353 B1* | 7/2020 | McLane | A61B 5/68 |
| 2008/0082017 A1* | 4/2008 | Savic | A61B 7/003 |
| | | | 600/529 |
| 2009/0232323 A1* | 9/2009 | Berk | A61B 7/026 |
| | | | 381/67 |
| 2018/0132815 A1* | 5/2018 | Tsai | A61B 5/42 |
| 2020/0146623 A1* | 5/2020 | Anushiravani | G06F 18/2148 |
| 2021/0030390 A1* | 2/2021 | Jeevannavar | A61B 5/7267 |
| 2021/0145306 A1* | 5/2021 | Karankevich | G16H 50/20 |
| 2023/0142937 A1* | 5/2023 | Jha | A61B 5/742 |
| | | | 600/586 |
| 2023/0255586 A1* | 8/2023 | Takeshima | H04R 1/04 |
| | | | 381/67 |

FOREIGN PATENT DOCUMENTS

| | | |
|---|---|---|
| KR | 10-0789705 B1 | 1/2008 |
| KR | 10-1072452 B1 | 10/2011 |
| KR | 10-2331753 B1 | 11/2021 |
| KR | 10-2502620 B1 | 2/2023 |

OTHER PUBLICATIONS

Korean Office Action dated Mar. 14, 2025 corresponding to application No. 10-2023-0048824.

* cited by examiner

FIG. 10C
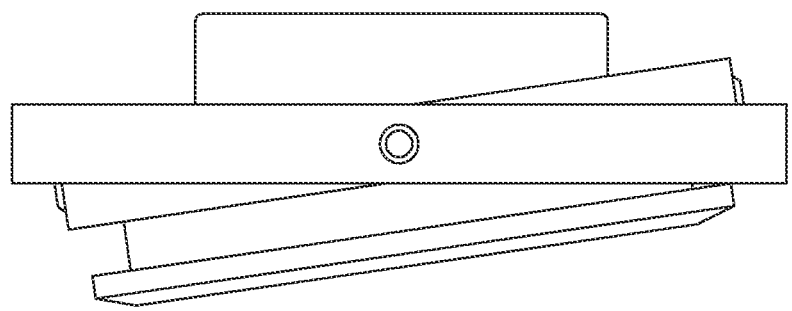
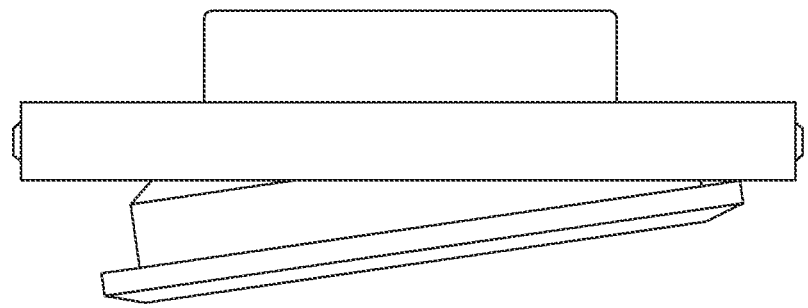
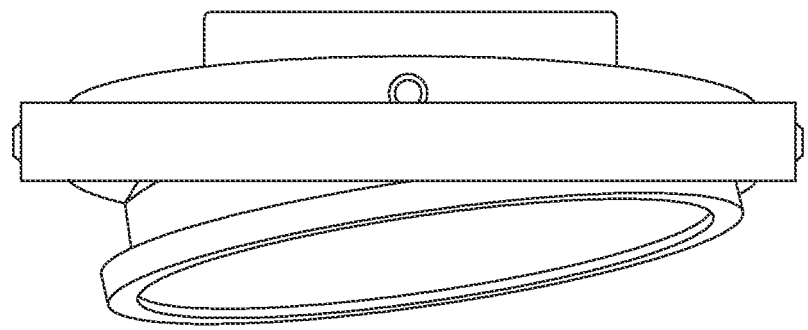

ELECTRONIC DEVICE FOR AUSCULTATION AND METHOD OF OPERATION THEREOF

RELATED APPLICATION(S)

This application claims the benefit of Korean Patent Application No. 10-2023-0048824, filed on Apr. 13, 2023, in the Korean Intellectual Property Office, the disclosure of which is incorporated herein by reference.

BACKGROUND

Technical Field

Example embodiments relate to an electronic device that performs an operation of obtaining auscultation sound data of a target and an operation of analyzing abnormalities in the auscultation sound data using an artificial intelligence (AI) model, and a method of operating the same.

Background Art

As the use of the Internet becomes more widespread and the human lifespan increases, interest in the home healthcare market is increasing. The home healthcare refers to a service in which medical management, treatment and support are provided remotely from the user's home without the user visiting a hospital.

Specifically, a service receiving attention and gaining popularity is a service that measures the auscultation sound of body parts such as the heart, lungs, or intestines using products such as a portable auscultator, diagnoses disease and provides information on the presence or absence of disease based on the measured auscultation sound.

Existing portable auscultators cannot directly analyze the abnormality of the obtained auscultation sound data, and thus an external device must be used to analyze abnormalities in auscultation sound data. Accordingly, communication failure or errors may occur due to communication failure between the portable auscultator and the external device, and personal information may be leaked.

SUMMARY

An aspect provides an electronic device for auscultation and a method of operating the same. More specifically, provided is an electronic device that performs an operation of obtaining auscultation sound data of a target and an operation of analyzing abnormalities in the auscultation sound data using an AI model, and a method of operating the same.

The technical tasks to be achieved by the present example embodiments are not limited to the technical tasks described above, and other technical tasks may be inferred from the following example embodiments.

According to an aspect, there is provided an electronic device including a housing with a handle that is formed on one part of the housing, a display that is positioned on another part of the housing and placed on one surface side of the housing, a sound collecting part that is positioned on the other part of the housing and placed on another surface side of the housing, and a controller that is configured to input first auscultation sound data obtained through the sound collecting part into a first artificial intelligence (AI) model and obtain an abnormality analysis result corresponding to the first auscultation sound data, and provide the abnormality analysis result through the display.

According to an example embodiment, for each set section of the first auscultation sound data, the abnormality analysis result may include information about probability that auscultation sound corresponding to the each set section is an abnormal sound.

According to an example embodiment, the first auscultation sound data may include heart sound data, and the information about probability that the auscultation sound is an abnormal sound may include information about probability that the auscultation sound is a normal sound and information about probability that the auscultation sound is heart murmur.

According to an example embodiment, the first auscultation sound data may include lung sound data, and the information about probability that the auscultation sound is an abnormal sound may include information about probability that the auscultation sound is a normal sound, information about probability that the auscultation sound is crackle, and information about probability that the auscultation sound is wheeze.

According to an example embodiment, the controller may be configured to provide information about a section where the probability that the auscultation sound is an abnormal sound is greater than or equal to a set value, among set sections of the first auscultation sound data through the display.

According to an example embodiment, the abnormality analysis result may include information about probability that auscultation sound is an abnormal sound corresponding to an entire section of the first auscultation sound data.

According to an example embodiment, the abnormality analysis result may include at least one piece of disease information corresponding to the first auscultation sound data.

According to an example embodiment, the electronic device may further include an audio output part, and an input part to obtain a user input, wherein the controller is configured to obtain a first user input to obtain auscultation sound data through the input part, obtain second auscultation sound data through the sound collecting part, output the second auscultation sound data through the audio output part, obtain a second user input to analyze auscultation sound data through the input part, obtain the first auscultation sound data for a set period of time from a time point that the second user input is obtained through the sound collecting part, and input the obtained first auscultation sound data into the first AI model.

According to an example embodiment, the controller may be configured to provide a graph corresponding to the second auscultation sound data through the display.

According to an example embodiment, the controller may be configured to input the first auscultation sound data into a second AI model to remove noise included in the first auscultation sound data, and input the first auscultation sound data from which the noise is removed into the first AI model to obtain the abnormality analysis result.

According to an example embodiment, the first auscultation sound data may include heart sound data, and the controller may be configured to input the heart sound data into a third AI model to obtain at least one of information about heart beat regularity corresponding to the heart sound data and information about heart rate corresponding to the heart sound data, and provide at least one of the information about heart beat regularity and the information about heart rate through the display.

According to an example embodiment, the first auscultation sound data may include lung sound data, and the controller may be configured to input the lung sound data into a fourth AI model to obtain at least one of information about respiratory regularity corresponding to the lung sound data and information about respiratory rate corresponding to the lung sound data, and provide at least one of the information about respiratory regularity and the information about respiratory rate through the display.

According to an example embodiment, the electronic device may further include an input part for obtaining a user input, and the controller may be configured to obtain auscultation position data through the input part, and input the first auscultation sound data and the auscultation position data into the first AI model to obtain the abnormality analysis result corresponding to the first auscultation sound data.

According to an example embodiment, the controller may be configured to, to obtain the auscultation position data, provide one or more auscultable positions through the display, and obtain a user input for selecting at least one auscultable position among the one or more auscultable positions through the input part.

According to an example embodiment, the electronic device may further include an image sensor, and the controller may be configured to obtain biometric data about an auscultation target through the image sensor, and input the first auscultation sound data and the biometric data into the first AI model to obtain the abnormality analysis result corresponding to the first auscultation sound data.

According to an example embodiment, the electronic device may further include a temperature sensor, and the controller may be configured to obtain body temperature data of the auscultation target through the temperature sensor, and input the first auscultation sound data and the body temperature data into the first AI model to obtain the abnormality analysis result corresponding to the first auscultation sound data.

According to an example embodiment, the sound collecting part may be configured to be tilted according to curvature of a body part with which the sound collecting part contacts.

According to an example embodiment, the sound collecting part may comprise a first axis bracket, a second axis bracket that is connected to the first axis bracket and rotates in a vertical direction of a first axis, and a diaphragm module that is connected to the second axis bracket and rotates in a vertical direction of a second axis, wherein the second axis bracket and the diaphragm module may rotate in order for diaphragm to come into close contact with the body part as the electronic device moves.

Additional aspects of example embodiments will be set forth in part in the description which follows and, in part, will be apparent from the description, or may be learned by practice of the disclosure.

According to example embodiments, it is possible to minimize obtained noise as a handle is formed on one part of housing of the electronic device and the sound collecting part is positioned on another part of the housing resulting in that the user's hand and a sound collecting part are relatively far apart.

Further, according to an example embodiment, by a display being placed on one surface side of the electronic device and the sound collecting part being placed on another surface side of the electronic device, a user may auscultate a target while viewing visual information such as a graph corresponding to auscultation sound data or abnormality analysis results provided through the display.

Further, according to an example embodiment, by the electronic device directly performing both an operation of obtaining auscultation sound data of a target and an operation of analyzing abnormalities in the auscultation sound data using an AI model, the data transmitting and receiving process between a device that obtains the auscultation sound data and a device that analyzes the auscultation sound data may be omitted. Accordingly, communication obstacles between the device obtaining the auscultation sound data and the device analyzing the auscultation sound data may disappear, and the risk of personal information such as auscultation sound data being leaked may be reduced. Further, as the process of reducing the sampling frequency of sound is omitted in the data transmitting and receiving process, the AI model may output accurate abnormality analysis results based on better quality auscultation sound data.

Further, according to an example embodiment, by the electronic device outputting obtained auscultation sound data or providing a graph corresponding to the auscultation sound data, a user may more accurately and conveniently find a position where biological sounds can be heard clearly by using the electronic device. Further, as the electronic device outputs the obtained auscultation sound data, or provides a graph corresponding to the auscultation sound data and at the same time provides an abnormality analysis result, the user may more accurately identify abnormalities in the auscultation sound data.

Further, according to an example embodiment, as the electronic device obtains auscultation sound analysis result using an AI model, decreased accuracy that may occur as the biological sounds of a target with a disease are different from those of a normal person may be resolved.

Further, according to an example embodiment, by the electronic device using an AI model trained based on auscultation position data as well as auscultation sound data, when the auscultation sound data and the auscultation position data are entered, the probability that the auscultation sound is an abnormal sound or what disease a user has may be determined with higher accuracy.

Further, according to an example embodiment, by the electronic device using an AI model trained based on biometric data as well as auscultation sound data, when the auscultation sound data and the biometric data are entered, the probability that the auscultation sound is an abnormal sound or what disease the user has may be determined with higher accuracy.

Further, according to an example embodiment, by a sound collecting part of the electronic device tilting according to the curvature of the body part of a target, the quantity of the obtained auscultation sound data may be improved. Specifically, when auscultating an anterior chest of a woman which is typically curvy or a target with the thin body, or when the appropriate arm angle of a user is not secured due to obstacles such as clothing, a user may more conveniently auscultate the target by using the electronic device.

Additional features and advantages of the invention will be set forth in the description which follows, and in part will be apparent from the description, or may be learned by practice of the invention. The objectives and other advantages of the invention will be realized and attained by the structure particularly pointed out in the written description and claims hereof as well as the appended drawings.

BRIEF DESCRIPTION OF THE DRAWINGS

These and/or other aspects, features, and advantages of the invention will become apparent and more readily appreciated from the following description of example embodiments, taken in conjunction with the accompanying drawings of which.

Figure 11:
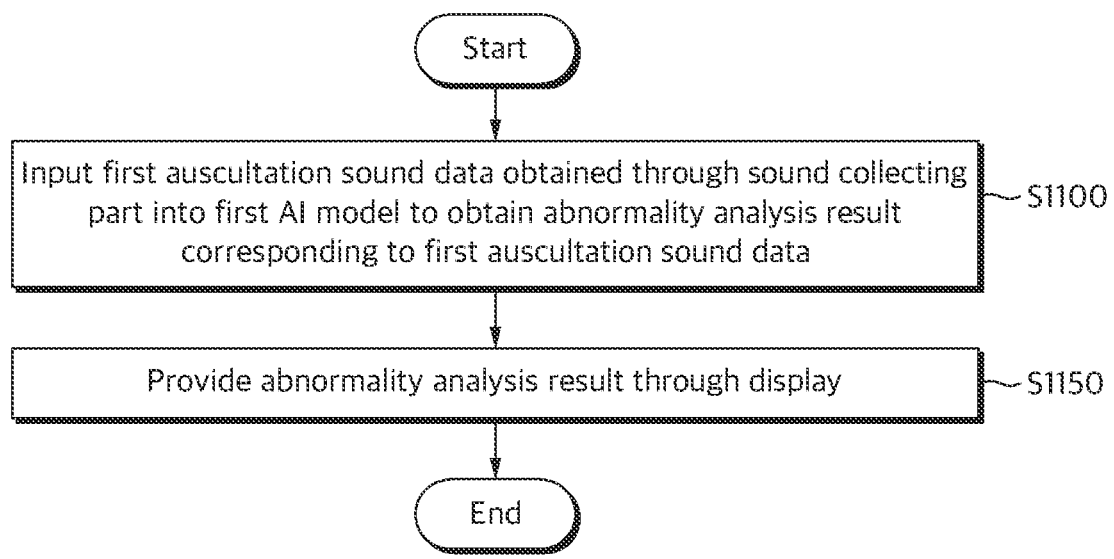
Figure 12:
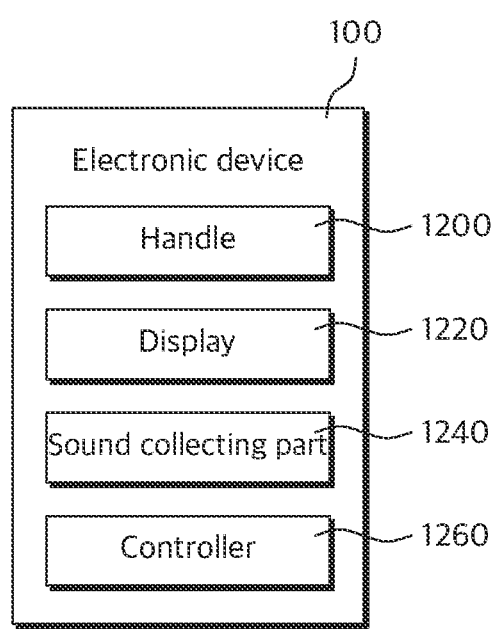

FIGS. TOA-TOD illustrate an example of components of a sound collecting part of an electronic device according to an example embodiment;

FIG. 11 shows a flowchart of a method of operating an electronic device according to an example embodiment; and FIG. 12 shows a block diagram of an electronic device according to an example embodiment.

DETAILED DESCRIPTION

Terms used in the example embodiments are selected from currently widely used general terms when possible while considering the functions in the present disclosure. However, the terms may vary depending on the intention or precedent of a person skilled in the art, the emergence of new technology, and the like. Further, in certain cases, there are also terms arbitrarily selected by the applicant, and in the cases, the meaning will be described in detail in the corresponding descriptions. Therefore, the terms used in the present disclosure should be defined based on the meaning of the terms and the contents of the present disclosure, rather than the simple names of the terms.

Throughout the specification, when a part is described as "comprising or including" a component, it does not exclude another component but may further include another component unless otherwise stated.

Expression "at least one of a, b and c" described throughout the specification may include "a alone," "b alone," "c alone," "a and b," "a and c," "b and c" or "all of a, b and c."

In the present disclosure, a "terminal" may be implemented as, for example, a computer or a portable terminal capable of accessing a server or another terminal through a network. Here, the computer may include, for example, a notebook, a desktop computer, and/or a laptop computer which are equipped with a web browser. The portable terminal may be a wireless communication device ensuring portability and mobility, and include (but is not limited to) any type of handheld wireless communication device, for example, a tablet PC, a smartphone, a communication-based terminal such as international mobile telecommunication (IMT), code division multiple access (CDMA), W-code division multiple access (W-CDMA), long term evolution (LTE), or the like.

AI-related functions according to the present disclosure are operated through a processor and a memory. The processor may consist of one or multiple processors. Here, the one or more processors may be general-purpose processors such as CPU, AP, digital signal processor (DSP) and so on, dedicated graphics processor, such as GPU and vision processing unit (VPU), or AI-specific processors such as NPUs. The one or more processors control input data to be processed according to predefined operation rules or AI models stored in a memory. Alternatively, if the one or more processors are AI-specific processors, AI-specific processors may be designed with a hardware structure specialized for processing a specific AI model.

The predefined operations rules or the AI models are characterized by being created through learning. Here, "being created through learning" means that the basic AI model is trained using a large number of learning data by a learning algorithm, thereby creating a predefined operation rule or AI model set to perform the desired characteristics or purposes. Such training may also be accomplished in the device itself on which AI according to the present disclosure is performed, or may be accomplished through a separate server and/or system. Examples of learning algorithms include supervised learning, unsupervised learning, semi-supervised learning and reinforcement learning, but the learning algorithms are not limited thereto.

An AI model may be composed of a plurality of neural network layers. Each of the plurality of neural network layers has a plurality of weight values, and performs neural network calculations through calculations between the calculation results of the previous layer and a plurality of weight values. The plurality of weight values of the plurality of neural network layers may be optimized by the learning results of the AI model. For example, during the learning process, a plurality of weight values may be updated so that loss or cost values obtained from the AI model are reduced and minimized. Artificial neural network may include deep neural network (DNN), convolutional neural network (CNN), recurrent neural network (RNN), restricted Boltzmann machine (RBM), deep belief network (DBN), bidirectional recurrent deep neural network (BRDNN) and Deep Q-Networks, but the artificial neural network is not limited thereto.

Hereinafter, example embodiments of the present disclosure will be described in detail with reference to the accompanying drawings so that those of ordinary skill in the art to which the present disclosure pertains may easily implement them. However, the present disclosure may be implemented in multiple different forms and is not limited to the example embodiments described herein.

Hereinafter, example embodiments will be described in detail with reference to the drawings.

Figure 1:
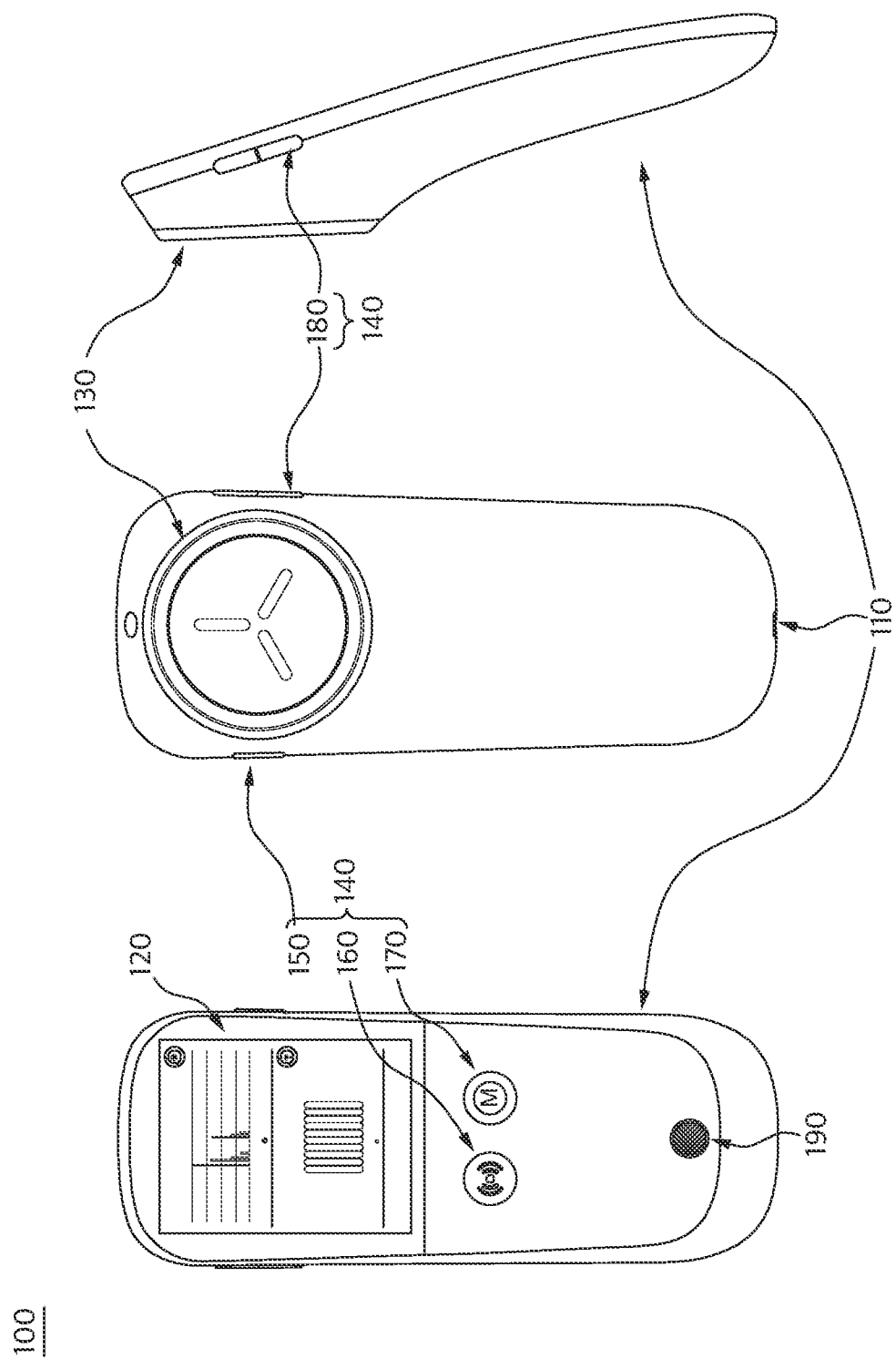
FIG. 1 illustrates an electronic device according to an example embodiment.

FIG. 1 shows an electronic device 100 according to an example embodiment.

FIG. 1 illustrates examples of the external appearance of the electronic device 100. Specifically, FIG. 1 illustrates one surface side, another surface side and the other side of the electronic device 100 from the left.

Referring to FIG. 1, the electronic device 100 may include a handle 110, a display 120, a sound collecting part 130, input parts 140 and an audio output part 190. Meanwhile, the electronic device 100 shown in FIG. 1 shows only elements related to the example embodiments. Therefore, those skilled in the art can understand that other general-purpose elements may be included in addition to the elements shown in FIG. 1.

For example, the electronic device 100 may further include an image sensor or a temperature sensor in addition to the elements illustrated in FIG. 1. Further, elements such as a controller and a communication part may be placed inside the housing of the electronic device 100.

According to an example embodiment, as an element for a user to hold when using the electronic device 100, the handle 110 may be formed on one part of the housing of the electronic device 100. In other words, the part of housing of the electronic device 100 may function as the handle 110. Meanwhile, the handle 110 may have a curved shape as illustrated in FIG. 1, but that is only an example embodiment. The handle 110 may have various shapes that allow the user to hold it more conveniently.

According to an example embodiment, as an element for providing various visual information to the user, the display 120 may be positioned on another part of the housing and be placed on one surface side of the housing. For example, the display 120 may provide the user with a graph corresponding to the obtained auscultation sound data or the results of analyzing the obtained auscultation sound data.

According to an example embodiment, as an element for obtaining biological signals of a target, the sound collecting part 130 may be positioned on the other part of the housing and be placed on another surface side of the housing. For example, the sound collecting part may obtain vibration or sound transmitted through the skin or clothing of a target, and convert the vibration or sound into an electrical signal.

Meanwhile, the surface side where the display 120 is placed and the other surface side where the sound collecting part 130 is placed may form an angle different from what is shown in FIG. 1. For example, FIG. 1 shows that the surface side on which the display 120 is placed and the other surface side on which the sound collecting part 130 is placed to form an acute angle, but the illustration is only an example embodiment. The surface side where the display 120 is placed and the other surface side where the sound collecting part 130 is placed may be parallel.

According to an example embodiment, the input parts 140 may include one or more input buttons 150, 160, 170 and 180 for obtaining a user input. For example, the input button 150 may obtain a user input for turning on or off the electronic device 100. The input button 160 may obtain a user input for obtaining or analyzing auscultation sound data. The input button 170 may obtain a user input regarding which body organ the user wishes to diagnose a disease among the heart, lungs or intestines, and so on. The input button 180 may obtain a user input to adjust the volume of the output auscultation sound data.

Further, the number, function, position and shape of one or more input buttons 150, 160, 170 and 180 included in the input parts 140 may be implemented differently from those described above. For example, one input button may perform a plurality of functions described above, or the one or more input buttons 150, 160, 170 and 180 may be arranged in a shape different from what is shown in FIG. 1 and may be arranged differently from what is shown in FIG. 1. Instead of being implemented in the form of an input button, the input parts 140 may be included in the display 120 to obtain a user input by a touch on the display 120.

According to an example embodiment, the audio output part 190 is an element for outputting auscultation sound data and may be placed on the part of the housing. For example, the audio output part 190 may output auscultation sound data obtained through the sound collecting part 130. Meanwhile, the audio output part 190 may be implemented in a shape different from what is shown in FIG. 1, and may be positioned on a different part.

As described above, as the handle 110 is formed on the part of the housing and the sound collecting part 130 is positioned on the other part of the housing, the user's hand and the sound collecting part 130 are relatively far apart, and the noise obtained may be minimized. For example, noise such as friction noise made when the user holds the handle 110 may be minimized.

Further, by the display 120 being placed on the surface side of the electronic device 100 and the sound collecting part 130 being placed on the other surface side of the electronic device 100, the user may auscultate the target while viewing visual information such as a graph corresponding to auscultation sound data or an abnormality analysis result provided through the display 120.

Figure 2:
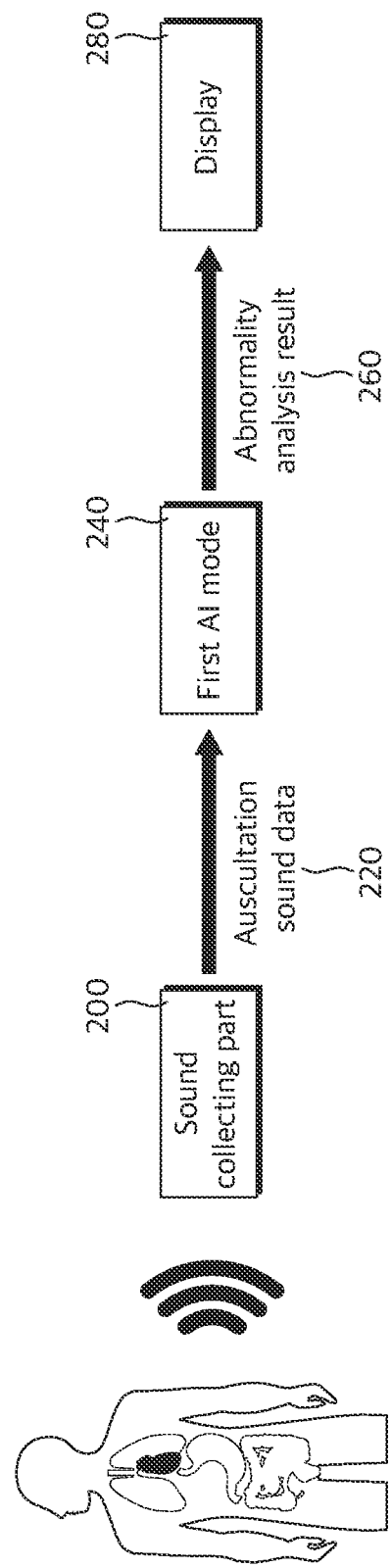
FIG. 2 is a diagram for explaining a method of operating an electronic device according to an example embodiment.

FIG. 2 is a diagram for explaining a method of operating the electronic device 100 according to an example embodiment.

According to an example embodiment, the electronic device 100 may obtain auscultation sound data 220 through a sound collecting part 200. More specifically, the user may contact the sound collecting part 200 of the electronic device 100 to the skin or clothing on the body part of the target to be examined, and the electronic device 100 may obtain vibration or sound transmitted through the skin or clothing, and based thereon, obtain the auscultation sound data 220.

For example, if the user wishes to examine the heart of the target, the electronic device 100 may obtain vibration or sound transmitted through the skin or clothing over the heart of the target, and based thereon, obtain heart sound data. Alternatively, if the user wishes to examine the lungs of the target, the electronic device 100 may obtain vibration or sound transmitted through the skin or clothing over the lungs of the target, and based thereon, obtain lung sound data.

According to an example embodiment, the electronic device 100 may input the auscultation sound data 220 obtained through the sound collecting part 200 to a first AI model 240, and obtain an abnormality analysis result 260 corresponding to the auscultation sound data 220.

According to an example embodiment, for each set section of the auscultation sound data 220, the abnormality analysis result 260 may include information about the probability that the auscultation sound corresponding to each set section is an abnormal sound. For example, if the auscultation sound data 220 is heart sound data, the abnormality analysis result 260 may include information about the probability that the heart sound corresponding to each set section is a normal sound and information about the probability that the heart sound is a heart murmur. Alternatively, if the auscultation sound data 220 is lung sound data, the abnormality analysis result 260 may include information about the probability that the lung sound corresponding to each set section is a normal sound, information about the probability that the lung sound is a crackle sound, and information about the probability that the lung sound is a wheeze sound.

According to an example embodiment, the abnormality analysis result 260 may include information about the probability that the auscultation sound corresponding to the entire section of the auscultation sound data 220 is an abnormal sound. For example, if the auscultation sound data 220 is heart sound data, the abnormality analysis result 260 may include information about the probability that the heart sound corresponding to the entire section is a normal sound and information about the probability that the heart sound is a heart murmur. Alternatively, if the auscultation sound data 220 is lung sound data, the abnormality analysis result 260 may include information about the probability that the lung sound corresponding to the entire section is a normal sound, information about the probability that the lung sound is a crackle sound and information about the probability that the lung sound is a wheeze sound.

According to an example embodiment, the abnormality analysis result 260 may include at least one piece of disease information corresponding to the auscultation sound data 220. For example, if the auscultation sound data 220 is heart sound data, the abnormality analysis result 260 may include information about heart disease that the target is diagnosed to have. Alternatively, if the auscultation sound data 220 is lung sound data, the abnormality analysis result 260 may include information about lung disease that the target is diagnosed as having.

Here, as an AI model that outputs abnormality analysis results based on the input auscultation sound data, the first AI model 240 may be trained based on a learning data set including one or more auscultation sound data and one or more disease data.

Further, the first AI model 240 may include a plurality of AI models each trained with different learning data depending on the body organ or specific part of the body organ to be diagnosed. For example, the first AI model 240 may include an AI model trained based on a learning data set including one or more intestine sound data and one or more intestine-related disease data. Alternatively, the first AI model 240 may include an AI model trained based on a learning data set containing one or more auscultation sound data measured for the pulmonic valve and one or more disease data for the pulmonic valve. As a result, the electronic device 100 may obtain the abnormality analysis result 260 using an appropriate AI model according to the type of the obtained auscultation sound data 220.

According to an example embodiment, the electronic device 100 may provide the abnormality analysis result 260 through a display 280. For example, on the display 280, the electronic device 100 may display information about the probability that an auscultation sound is an abnormal sound or at least one piece of disease information corresponding to the auscultation sound data 220. This will be described in detail with reference to FIGS. 7A to 7B and 8A to 8B.

As described above, by the electronic device 100 directly performing both the operation of obtaining auscultation sound data of a target and the operation of analyzing abnormalities in the auscultation sound data using an AI model, the data transmitting and receiving process between a device that obtains auscultation sound data and a device that analyzes the auscultation sound data may be omitted. Accordingly, communication failures between the device that obtains auscultation sound data and the device that analyzes the auscultation sound data may be eliminated, and the risk of personal information such as auscultation sound data being leaked may be reduced. Further, as the process of reducing the sound sampling frequency is omitted during the data transmitting and receiving process, the AI model may output more accurate abnormality analysis results based on better quality auscultation sound data.

Through the display 280, the electronic device 100 provides in real time the abnormality analysis result 260 corresponding to the auscultation sound data 220 of the target obtained through the sound collecting part 200, and the user may check the analysis result regarding an auscultation position in real time. As a result, in a situation where the user must move the device that obtains auscultation sound data and search for a position where biological sounds can be clearly heard for the reason that the position where biological sounds are clearly heard is different for each target, by using the electronic device 100, the user may more accurately and conveniently find a position where biological sounds can be clearly heard.

Figure 3:
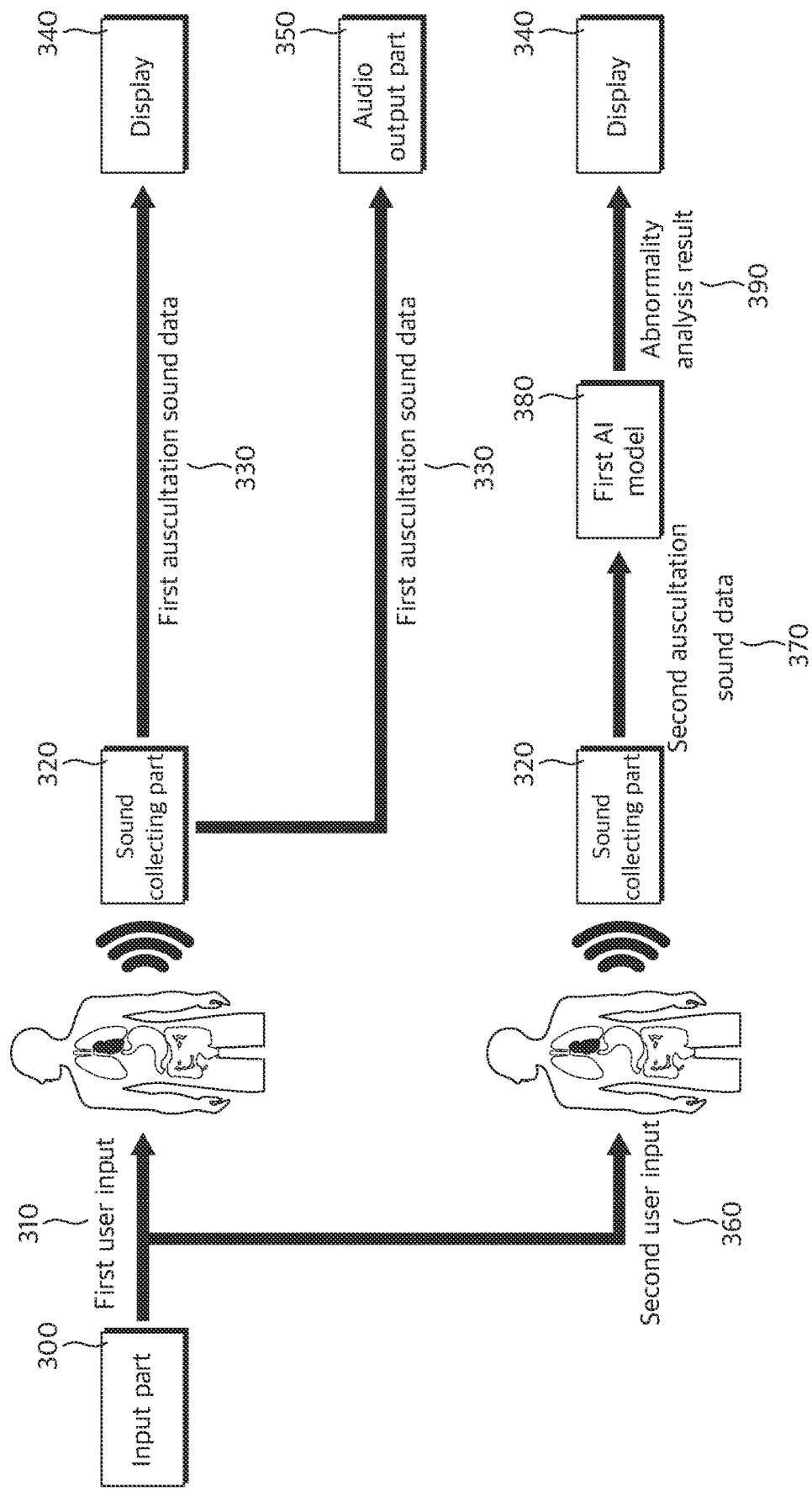
FIG. 3 is a diagram for explaining a method of operating an electronic device according to an example embodiment.

FIG. 3 is a diagram for explaining a method of operating the electronic device 100 according to an example embodiment. Content that overlaps with FIG. 2 will be briefly explained or omitted.

According to an example embodiment, the electronic device 100 may obtain a first user input 310 for obtaining auscultation sound data through an input part 300. For example, the electronic device 100 may obtain an input for selecting an auscultation button formed on the housing of the electronic device 100 of the user or an auscultation icon displayed on a display 340.

According to an example embodiment, as the first user input 310 is obtained, the electronic device 100 may obtain first auscultation sound data 330 through a sound collecting part 320. For example, as the user touches the sound collecting part 320 of the electronic device 100 on the body part of the target and then selects the auscultation button or the auscultation icon, the electronic device 100 may obtain vibration or sound transmitted through the body part, and based thereon, obtain the first auscultation sound data 330.

According to an example embodiment, the electronic device 100 may provide a graph corresponding to the first auscultation sound data 330 through the display 340. For example, if the first auscultation sound data 330 is heart sound data, the electronic device 100 may obtain a graph of the volume of the heart sound over time based on the heart sound data, and display the obtained graph on the display 340. Alternatively, if the first auscultation sound data 330 is lung sound data, the electronic device 100 may obtain a graph of the volume of the lung sound over time based on the lung sound data, and display the obtained graph on the display 340.

According to an example embodiment, the electronic device 100 may output the first auscultation sound data 330 through an audio output part 350. For example, the electronic device 100 may obtain the first auscultation sound data 330 through the sound collecting part 320, and the electronic device 100 may amplify the obtained first auscultation sound data 330 and output the first auscultation sound data 330 in real time through the audio output part 350.

According to an example embodiment, the electronic device 100 may obtain a second user input 360 for analyzing the auscultation sound data through the input part 300. For example, if the user determines that the graph displayed on the display 340 or the sound output through the audio output part 350 is abnormal, the electronic device 100 may obtain an input for selecting an analysis button formed on the housing of the electronic device 100 or an analysis icon displayed on the display 340 by the user.

According to an example embodiment, as the second user input 360 is obtained, the electronic device 100 may obtain second auscultation sound data 370 through the sound collecting part 320 for a set period of time from the time the second user input 360 is obtained. For example, as the user selects the analysis button or the analysis icon, the electronic device 100 may obtain vibration or sound for a set period of time from the time the analysis button or the analysis icon is selected, and based thereon, obtain the second auscultation sound data 370. Here, the set period of time may be set to a different value depending on the body organ that the user wishes to diagnose, and may be changed based on a user input.

According to an example embodiment, by inputting the second auscultation sound data 370 obtained through the sound collecting part 320 into a first AI model 380, the electronic device 100 may obtain an abnormality analysis result 390 corresponding to the second auscultation sound data 370. For example, by inputting the second auscultation sound data 370 into the first AI model 380, the electronic device 100 may obtain information about the probability that the auscultation sound corresponding to the second auscultation sound data 370 is an abnormal sound or at least one piece of disease information corresponding to the second auscultation sound data 370.

According to an example embodiment, the electronic device 100 may provide the abnormality analysis result 390 through the display 340. For example, on the display 340, the electronic device 100 may display information about the probability that an auscultation sound is an abnormal sound or at least one piece of disease information corresponding to the second auscultation sound data 370. This will be described in detail with reference to FIGS. 7A to 7B and 8A to 8B.

As described above, by the electronic device 100 outputting the obtained auscultation sound data or providing a graph corresponding to the auscultation sound data, by using the electronic device 100, the user may more accurately and conveniently find a position where biological sounds can be clearly heard. Further, as the electronic device 100 provides an abnormality analysis result and simultaneously outputs the obtained auscultation sound data or provides a graph corresponding to the auscultation sound data, the user may more accurately identify abnormalities in the auscultation sound data.

Figure 4:
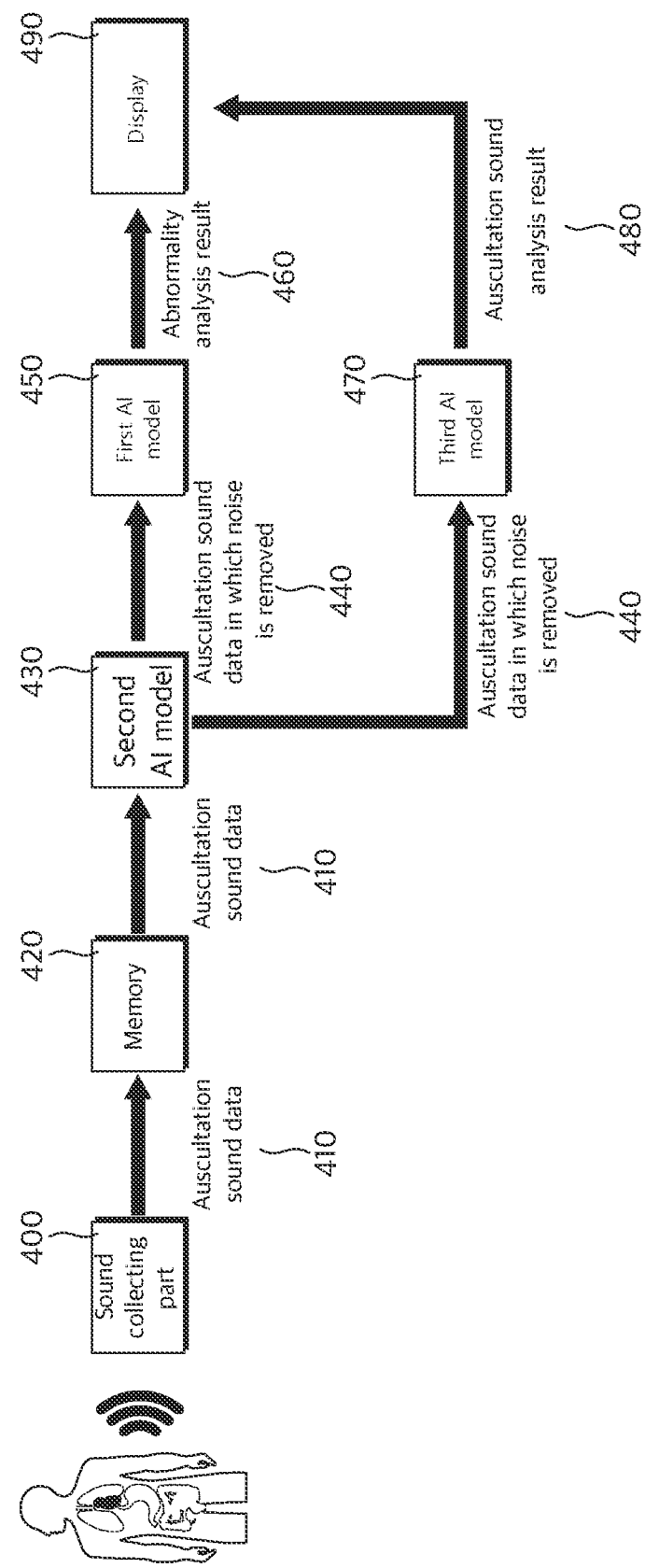
FIG. 4 is a diagram for explaining a method of operating an electronic device according to an example embodiment.

FIG. 4 is a diagram for explaining a method of operating the electronic device 100 according to an example embodiment. Content that overlaps with FIG. 2 will be briefly explained or omitted.

According to an example embodiment, the electronic device 100 may obtain auscultation sound data 410 through a sound collecting part 400. For example, the electronic device 100 may obtain vibration or sound transmitted through the skin or clothing on the body part of the target, and based thereon, obtain the auscultation sound data 410.

According to an example embodiment, the electronic device 100 may store the obtained auscultation sound data 410 in a memory 420. For example, when the electronic device 100 obtains a user input for analyzing auscultation sound data through the input part, the electronic device 100 may store in the memory 420 the auscultation sound data 410 obtained for a set period of time from the time the user input is obtained.

According to an example embodiment, the electronic device 100 may input the auscultation sound data 410 stored in the memory 420 to a second AI model 430 to remove noise included in the auscultation sound data 410. For example, by inputting the auscultation sound data 410 into the second AI model 430, noise such as friction sounds between the sound collecting part 400 and the skin included in the auscultation sound data 410, friction sound generated when the user holds the electronic device 100, ambient sounds such as speech and white noise may be removed.

Here, as an AI model that outputs auscultation sound data from which noise is removed based on the input auscultation sound data, the second AI model 430 may be trained based on a learning data set including one or more auscultation sound data.

According to an example embodiment, the electronic device 100 may input auscultation sound data 440 from which noise is removed into a first AI model 450 to obtain an abnormality analysis result 460. For example, the electronic device 100 may input the auscultation sound data 440 from which noise is removed into the first AI model 450, and may obtain information about the probability that the auscultation sound corresponding to the auscultation sound data 440 is an abnormal sound or at least one piece of disease information corresponding to the auscultation sound data 440.

According to an example embodiment, the electronic device 100 may input the auscultation sound data 440 from which noise is removed into a third AI model 470 to obtain an auscultation sound analysis result 480. For example, if the auscultation sound data 410 is heart sound data, the electronic device 100 may input heart sound data into the third AI model 470 to obtain at least one of information about heart beat regularity and information about heart rate. Alternatively, if the auscultation sound data 410 is lung sound data, the electronic device 100 may input lung sound data into the third AI model 470 to obtain at least one of information about respiratory regularity and information about respiratory rate.

Here, as an AI model that outputs auscultation sound analysis results based on input auscultation sound data, the third AI model 470 may be trained based on a learning data set including one or more auscultation sound data and auscultation sound analysis data.

Further, the third AI model 470 may include a plurality of AI models each trained with different learning data depending on the body organ or specific part of the body organ to be diagnosed. For example, the third AI model 470 may include an AI model trained based on the learning data set containing one or more lung sound data and one or more biometric data about the lungs. Alternatively, the third AI model 470 may include an AI model trained based on the learning data set containing one or more auscultation sound data measured about the heart and one or more biometric data about the heart. As a result, the electronic device 100 may obtain the auscultation sound analysis result 480 using an appropriate AI model according to the type of the obtained auscultation sound data 410.

According to an example embodiment, the electronic device 100 may provide the abnormality analysis result 460 and the auscultation sound analysis result 480 through a display 490. For example, if the auscultation sound data 410 is heart sound data, the electronic device 100 may provide at least one of information about the probability that an auscultation sound of the heart is an abnormal heart sound, information about heart beat regularity along with at least one piece of disease information about the heart and information about the heart rate through the display 490. Alternatively, if the auscultation sound data 410 is lung sound data, the electronic device 100 may provide at least one of information about the probability that auscultation sound of the lung is an abnormal sound, information about respiratory regularity corresponding to at least one piece of lung disease information and information about respiratory rate through the display 490.

As described above, as the electronic device 100 obtains an auscultation sound analysis result using an AI model, decreased accuracy that may occur as the biological sounds of a target with disease are different from those of a normal person may be resolved.

Figure 5:
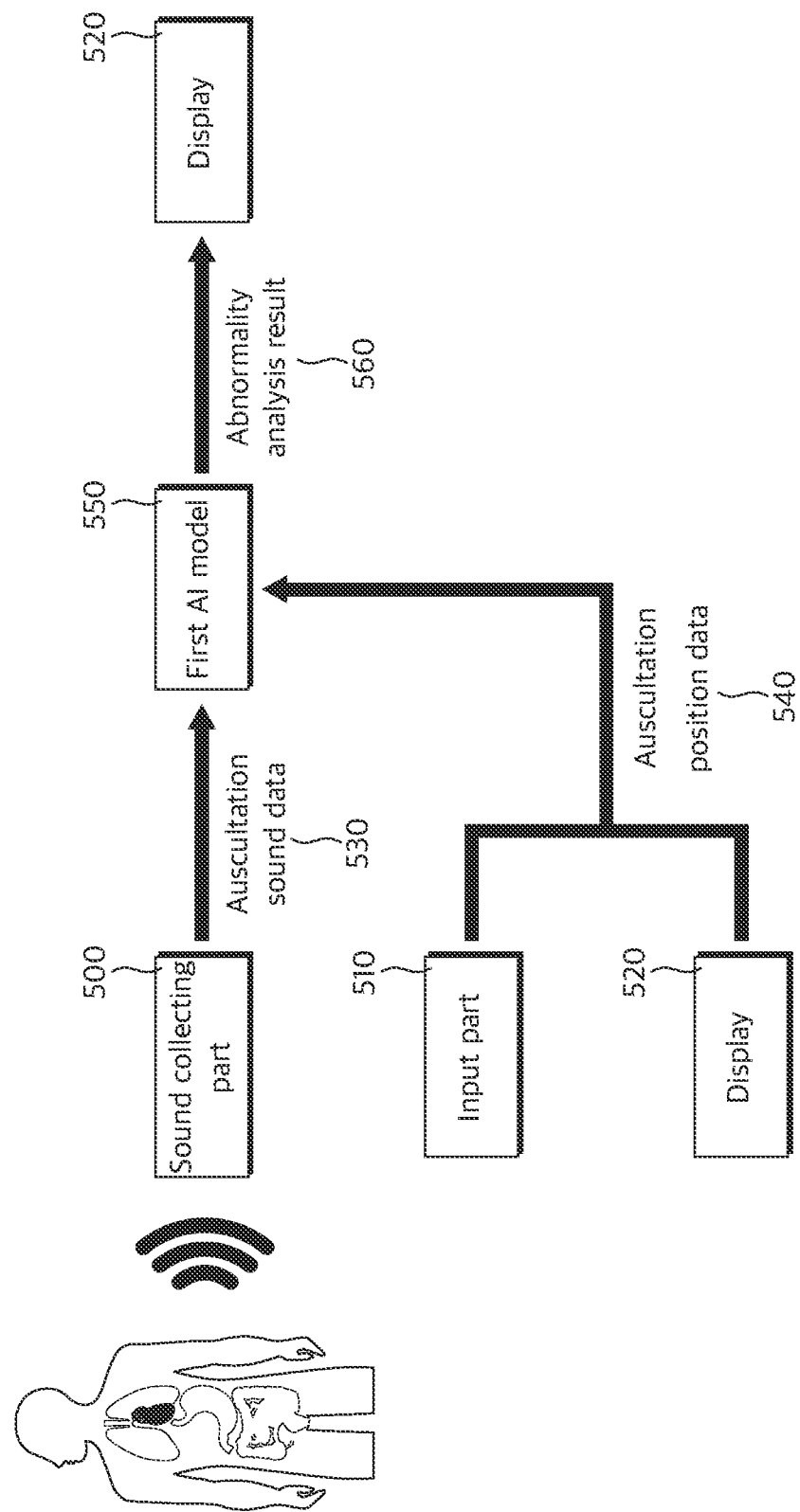
FIG. 5 is a diagram for explaining a method of operating an electronic device according to an example embodiment.

FIG. 5 is a diagram for explaining a method of operating the electronic device 100 according to an example embodiment. Content that overlaps with FIG. 2 will be briefly explained or omitted.

According to an example embodiment, the electronic device 100 may obtain auscultation sound data 530 through a sound collecting part 500. For example, the electronic device 100 may obtain vibration or sound transmitted through the skin or clothing on the body part of the target, and based thereon, obtain the auscultation sound data 530.

According to an example embodiment, the electronic device 100 may obtain setting data through an input part 510. For example, the electronic device 100 may obtain an input for selecting a setting value for which body organ disease the user wishes to be diagnosed with, such as the heart, lungs and intestines.

According to an example embodiment, the electronic device 100 may obtain auscultation position data 540 through the input part 510 and a display 520.

For example, the electronic device 100 may display one or more auscultable positions related to body organs according to setting data on the display 520, and the electronic device 100 may obtain a user input for selecting at least one auscultable positon among one or more auscultable positions through the input part 510. More specifically, if the body organ that the user wishes to diagnose is the heart, the electronic device 100 may display one or more positions where heart sounds can be auscultated on the display 520, and the electronic device 100 may obtain a user input for selecting at least one position where heart sound is auscultated among the positions where heart sound is auscultated. Alternatively, if the body organ that the user wishes to be diagnosed with is the lungs, the electronic device 100 may display one or more positions where lung sound is auscultated on the display 520, and the electronic device 100 may obtain a user input for selecting at least one position where lung sound is auscultated among the positions where lung sound is auscultated.

For another example, the electronic device 100 may display a human body model on the display 520, and may obtain a user input for selecting a specific body part on the human body model. However, the method by which the electronic device 100 obtains the auscultation position data 540 is not limited to the above example embodiments.

According to an example embodiment, by inputting the auscultation sound data 530 and the auscultation position data 540 into a first AI model 550, the electronic device 100 may obtain an abnormality analysis result 560 corresponding to the auscultation sound data 530. For example, by inputting the auscultation sound data 530 and the auscultation position data 540 into the first AI model 550, the electronic device 100 may obtain information about the probability that the auscultation sound corresponding to the auscultation sound data 530 is an abnormal sound or at least one piece of disease information corresponding to the auscultation sound data 530.

Here, as an AI model that outputs abnormality analysis results based on input auscultation sound data and auscultation position data, the first AI model 550 may be trained based on a learning data set including one or more auscultation sound data, one or more auscultation position data, and one or more disease data.

Meanwhile, the first AI model 550 may include a plurality of AI models each trained with different learning data depending on the body organ to be diagnosed. For example, the first AI model 550 may include an AI model trained based on a learning data set including one or more heart sound auscultation data, one or more data on heart sound auscultation position, and one or more heart disease data. Alternatively, the first AI model 550 may include an AI model trained based on a learning data set including one or more lung sound data, one or more data on lung sound auscultation positions and one or more disease data about lungs. As a result, the electronic device 100 may obtain the abnormality analysis result 560 using an AI model suitable for the type of auscultation sound data 530 based on the setting data.

According to an example embodiment, the electronic device 100 may provide the abnormality analysis result 560 through the display 520. For example, on the display 520, the electronic device 100 may display information about the probability that an auscultation sound is an abnormal sound or at least one piece of disease information corresponding to the auscultation sound data 530. This will be described in detail with reference to FIGS. 7A to 7B and 8A to 8B.

As described above, the electronic device 100 may use an AI model trained based on auscultation position data as well as auscultation sound data, and thus when auscultation sound data and auscultation position data are input, the probability that the auscultation sound is an abnormal sound or what disease the user has may be determined with higher accuracy.

Figure 6:
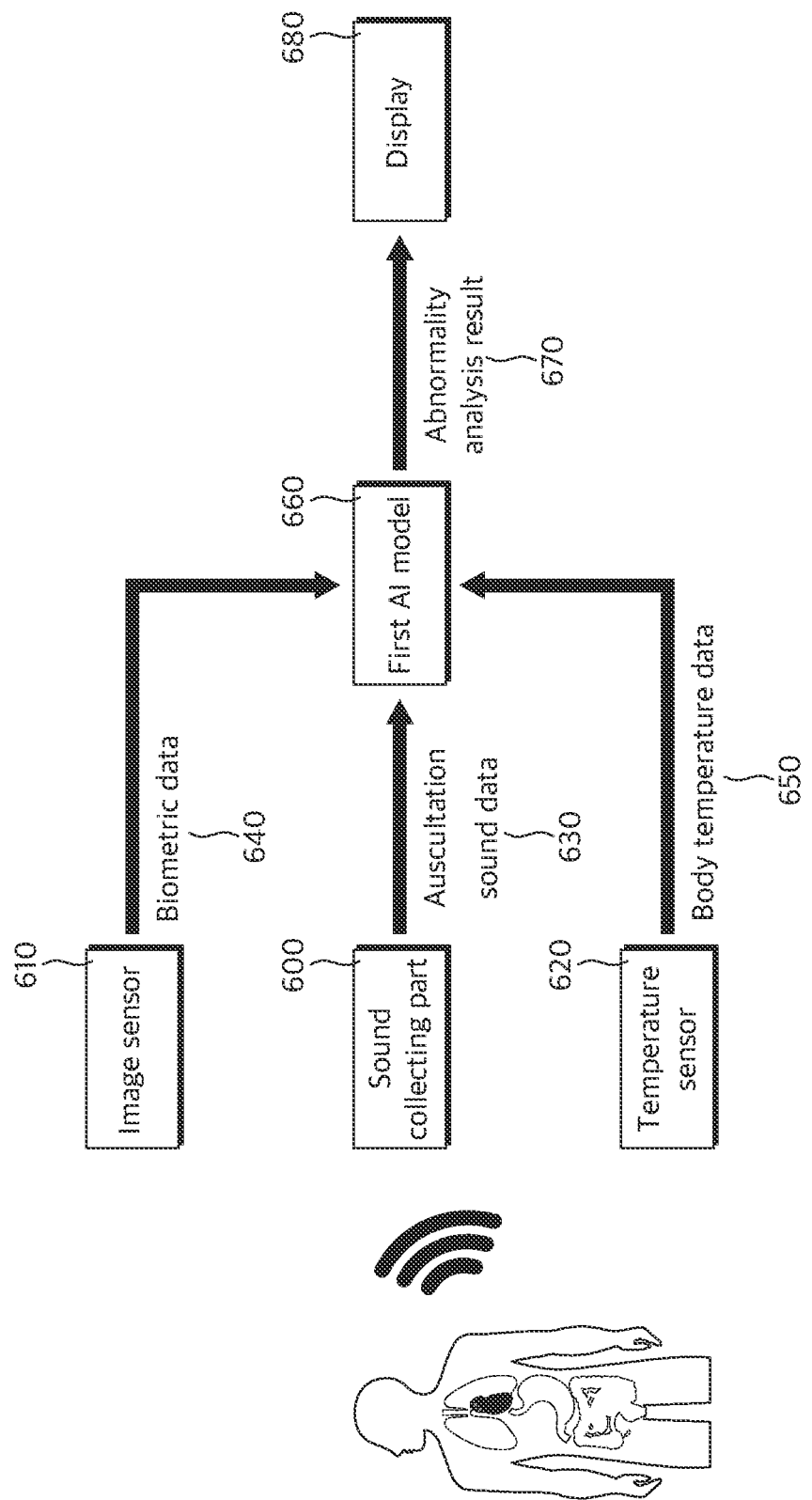
FIG. 6 is a diagram for explaining a method of operating an electronic device according to an example embodiment.

FIG. 6 is a diagram for explaining a method of operating the electronic device 100 according to an example embodiment. Content that overlaps with FIG. 2 will be briefly explained or omitted.

According to an example embodiment, the electronic device 100 may obtain auscultation sound data 630 through a sound collecting part 600. For example, the electronic device 100 may obtain vibration or sound transmitted through the skin or clothing on the body part of the target, and based thereon, obtain the auscultation sound data 630.

According to an example embodiment, the electronic device 100 may obtain biometric data 640 about the auscultation target through an image sensor 610. For example, the electronic device 100 may obtain the biometric data 640 about the auscultation target by reading a quick response (QR) code or barcode about the target through the image sensor 610. Here, the biometric data 640 may include at least one of heart beat regularity data, heart rate data, respiratory rate data, respiratory regularity data, body temperature data, age data, blood pressure data and blood sugar data.

According to an example embodiment, the electronic device 100 may obtain body temperature data 650 regarding the auscultation target through a temperature sensor 620. For example, the user may touch the temperature sensor 620 of the electronic device 100 on the body part of the target, and the electronic device 100 may obtain the body temperature data.

According to an example embodiment, with an input of at least one of the biometric data 640 and the body temperature data 650 and the auscultation sound data 630 into a first AI model 660, the electronic device 100 may obtain an abnormality analysis result 670 corresponding to the auscultation sound data 630. For example, with an input of at least one of the biometric data 640 and the body temperature data 650 and the auscultation sound data 630 into the first AI model 660, the electronic device 100 may obtain information about the probability that the auscultation sound corresponding to the auscultation sound data 630 is an abnormal sound or at least one piece of disease information corresponding to the auscultation sound data 630.

Here, as an AI model that outputs abnormality analysis results based on input auscultation sound data and biometric data, the first AI model 660 may be trained based on a learning data set including one or more auscultation sound data, one or more biometric data, and one or more disease data.

Meanwhile, the first AI model 550 may include a plurality of AI models each trained with different leaning data depending on the body organ to be diagnosed. For example, the first AI model 660 may include an AI model trained based on a learning data set including at least one of heart beat regularity data, heart rate data, body temperature data, age data, blood pressure data and blood sugar data, one or more heart sound data and one or more heart-related disease data. Alternatively, the first AI model 660 may include an AI model trained based on a learning data set including at least one of respiratory rate data, respiratory regularity data, body temperature data, age data, blood pressure data and blood sugar data, one or more lung sound data and one or more lung-related disease data. As a result, the electronic device 100 may obtain the abnormality analysis result 670 using an appropriate AI model according to the type of the obtained auscultation sound data 630. In this example embodiment, the first AI model is a one dimensional convolutional neural network. One dimensional convolutional neural networks achieve the state-of-the-art performance levels in applications such as personalized biomedical data classification and early diagnosis, structural health monitoring, and anomaly detection. Another major advantage is that a real-time and low-cost hardware implementation is feasible due to the simple and compact configuration of 1D CNNs that perform only 1D convolutions (scalar multiplications and additions).

According to an example embodiment, the electronic device 100 may provide the abnormality analysis result 670 through a display 680. For example, on the display 680, the electronic device 100 may display information about the probability that an auscultation sound is an abnormal sound or at least one piece of disease information corresponding to the auscultation sound data 630. This will be described in detail with reference to FIGS. 7A, 7B, 8A and 8B.

As described above, by the electronic device 100 using the AI model trained based on biometric data as well as the auscultation sound data, when auscultation sound data and biometric data are input, the probability that the auscultation sound is an abnormal sound or what disease the user has may be determined with higher accuracy.

Figure 7A:
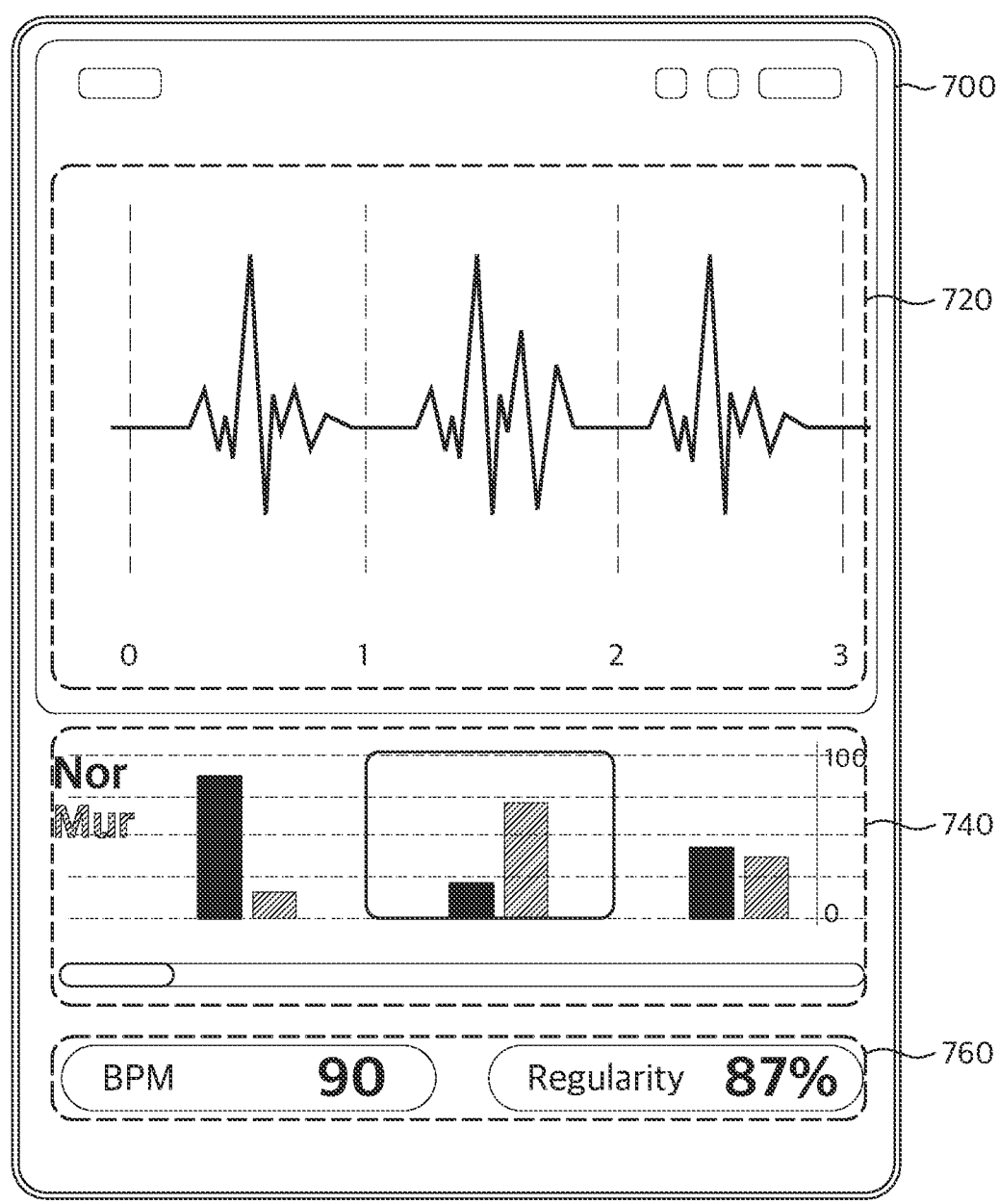
FIGS. 7A and 7B show a user interface (UI) provided through an electronic device through a display.
Figure 7B:
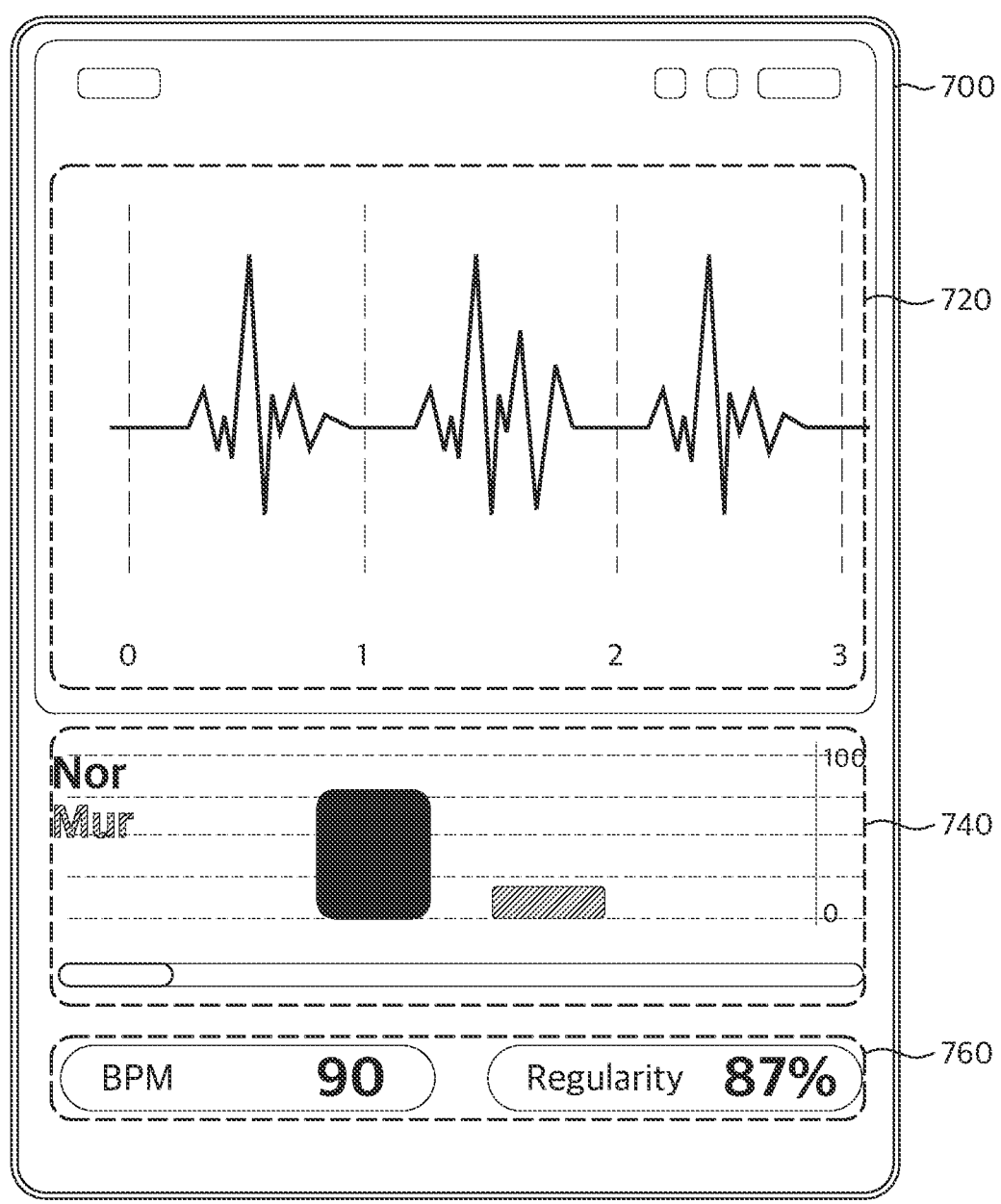

FIGS. 7A and 7B show a UI 700 provided through the electronic device 100 through a display.

According to an example embodiment, the UI 700 may include at least one of an area 720 for displaying a graph corresponding to auscultation sound data, an area 740 for displaying an abnormality analysis result and an area 760 for displaying auscultation sound analysis result.

According to an example embodiment, the electronic device 100 may display a graph corresponding to auscultation sound data in the area 720. For example, if the auscultation sound data obtained through a sound collecting part is heart sound data, the electronic device 100 may obtain a graph of the volume of the heart sound over time based on the heart sound data, and display the obtained graph in the area 720.

According to an example embodiment, the electronic device 100 may display the abnormality analysis result corresponding to the auscultation sound data in the area 740.

Referring to FIG. 7A, for each set section of auscultation sound data, the electronic device 100 may display information about the probability that the auscultation sound corresponding to each set section is an abnormal sound in the area 740. For example, if the auscultation sound data obtained through the sound collecting part is heart sound data, the electronic device 100 may display information about the probability that the heart sound corresponding to each set section is a normal sound and information about the probability that the heart sound is a heart murmur in the area 740. More specifically, for each set section, the electronic device 100 may display the probability that the heart sound corresponding to a set section is a normal sound on the left side bar, and the probability that the heart sound corresponding to the set section is a heart murmur on the right side bar.

Here, among the set sections of the auscultation sound data, the electronic device 100 may display information about a section where the probability that the auscultation sound is an abnormal sound is greater than a set value in the area 740. For example, as it is identified that the probability that the heart sound corresponding to the second section of the heart sound data is a heart murmur is greater than or equal to the set value, the electronic device 100 may display the second section as a yellow box.

As above, for each set section, the electronic device 100 provides information about the probability that the auscultation sound corresponding to each set section is an abnormal sound and information about a section where the probability that the auscultation sound is an abnormal sound is greater than or equal to the set value, and thus the user may more conveniently and easily check in which section abnormal sound is detected.

Referring to FIG. 7B, in the area 740, the electronic device 100 may display information about the probability that the auscultation sound corresponding to the entire section of the auscultation sound data is an abnormal sound. For example, if the auscultation sound data obtained through the sound collecting part is heart sound data, the electronic device 100 may display information about the probability that the heart sound corresponding to the entire section is a normal sound and information about the probability that the heart sound corresponding to the entire section is a heart murmur in the area 740. Here, the probability that the auscultation sound corresponding to the entire section is an abnormal sound may represent the average value of the probabilities corresponding to all sections that the auscultation sound is an abnormal sound, but the probability corresponding to the entire section is not limited thereto.

Further, the electronic device 100 may display at least one piece of disease information corresponding to auscultation sound data in the area 740. For example, if the auscultation sound data obtained through the sound collecting part is heart sound data, the electronic device 100 may display information about disease heart that the target is diagnosed to have in the area 740.

According to an example embodiment, the electronic device 100 may display the auscultation sound analysis result corresponding to the auscultation sound data in the area 760. For example, if the auscultation sound data obtained through the sound collecting part is heart sound data, the electronic device 100 may display at least one of information about heart beat regularity and information about heart rate corresponding to the heart sound data in the area 760.

Figure 8A:
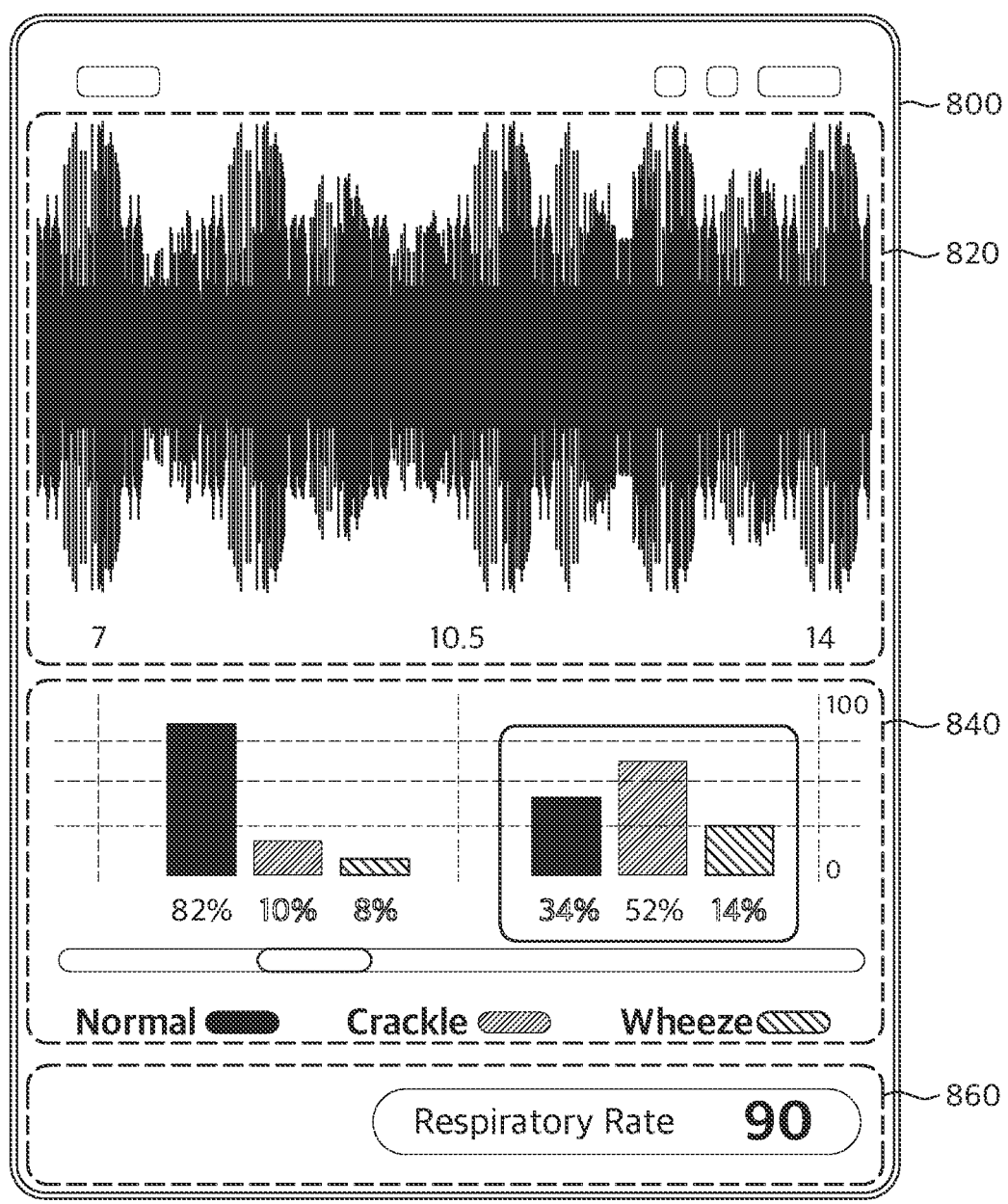
FIGS. 8A and 8B show a UI provided through an electronic device through a display.
Figure 8B:
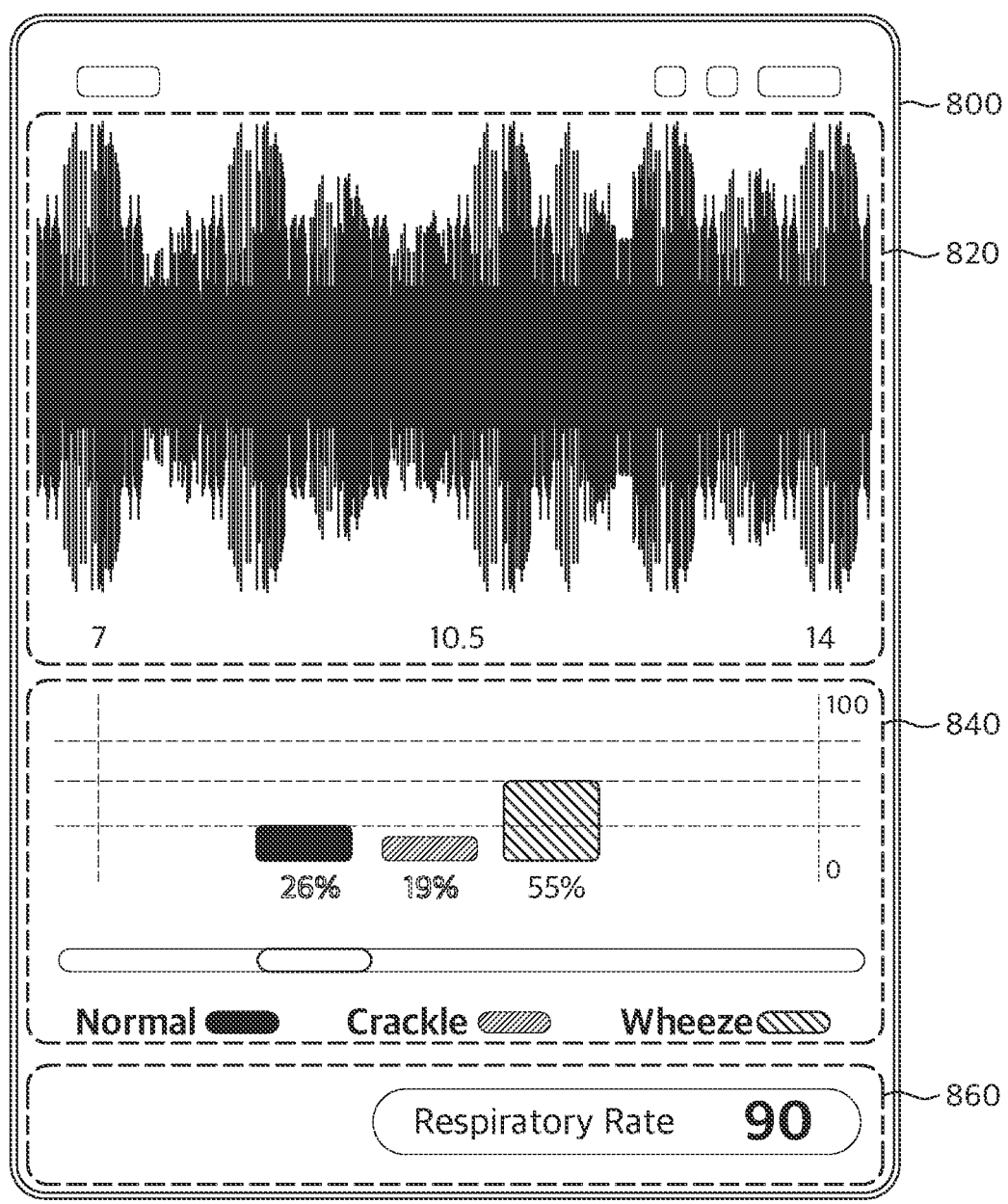

FIGS. 8A and 8B show a UI 800 provided through the electronic device 100 through a display.

According to an example embodiment, the UI 800 may include at least one of an area 820 for displaying a graph corresponding to auscultation sound data, an area 840 for displaying an abnormality analysis result, and an area 860 for displaying an auscultation sound analysis result.

According to an example embodiment, the electronic device 100 may display a graph corresponding to auscultation sound data in the area 820. For example, if the auscultation sound data obtained through the sound collecting part is lung sound data, the electronic device 100 may obtain a graph of the volume of lung sound over time based on the lung sound data, and display the obtained graph in the area 820.

According to an example embodiment, the electronic device 100 may display the abnormality analysis result corresponding to the auscultation sound data in the area 840.

Referring to FIG. 8A, for each set section of the auscultation sound data, the electronic device 100 may display information about the probability that the auscultation sound corresponding to each set section is an abnormal sound in the area 840. For example, if the auscultation sound data obtained through the sound collecting part is lung sound data, the electronic device 100 may display information about the probability that the lung sound corresponding to the set sections is a normal sound, information about the probability that the lung sound is crackle, and information about the probability that the lung sound is wheeze. More specifically, for each set section, the electronic device 100 may indicate the probability that the lung sound corresponding to the set sections is a normal sound as a left side bar, and indicate the probability that the lung sound is crackle as a bar in the middle, and indicate the probability that the lung sound is wheeze as a right side bar.

Here, among the set sections of the auscultation sound data, the electronic device 100 may display information about a section where the probability that the auscultation sound is an abnormal sound is greater than or equal to a set value in the area 840. For example, as it is identified that the probability that the lung sound corresponding to a second section of the lung sound data is crackle is greater than or equal to a set value, the electronic device 100 may display the second section as a yellow box.

As such, for each set section, the electronic device 100 provides information about the probability that the auscultation sound corresponding to the set section is an abnormal sound and information about a section where the probability that the auscultation sound is an abnormal sound is greater than or equal to the set value, and thus the user may more conveniently and easily check in which section abnormal sound is detected.

Referring to FIG. 8B, the electronic device 100 may display information about the probability that the auscultation sound corresponding to the entire section of auscultation sound data is an abnormal sound in the area 840. For example, if the auscultation sound data obtained through the sound collecting part is lung sound data, the electronic device 100 may display information about the probability that the lung sound corresponding to the entire section is a normal sound, information about the probability that lung sound is crackle, and information about the probability that the lung sound is wheeze in the area 840. Here, the probability that the auscultation sound corresponding to the entire section is an abnormal sound may represent the average value of the probabilities corresponding to all sections that the auscultation sound is an abnormal sound, but the probability corresponding to the entire section is not limited thereto.

Further, the electronic device 100 may display at least one piece of disease information corresponding to the auscultation sound data in the area 840. For example, if the auscultation sound data obtaining through the sound collecting part is lung sound data, the electronic device 100 may display information about disease lung that the target is diagnosed to have in the area 840.

According to an example embodiment, the electronic device 100 may display the auscultation sound analysis result corresponding to the auscultation sound data in the area 860. For example, if the auscultation sound data obtained through the sound collecting part is lung sound data, the electronic device 100 may display at least one of information on respiratory regularity corresponding to the lung sound data and information about respiratory rate in the area 860.

Figure 9:
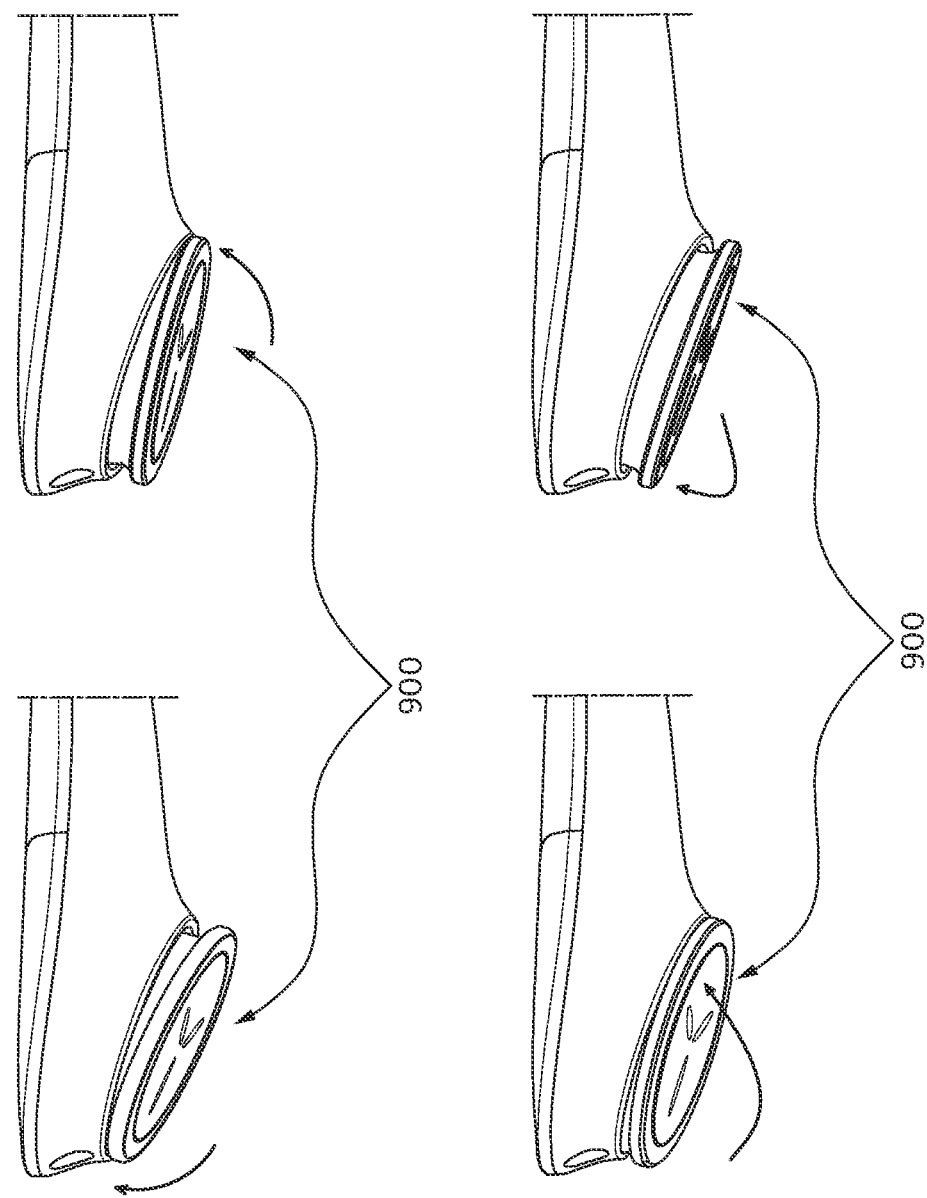
FIG. 9 shows tilting operations of a sound collecting part of an electronic device according to an example embodiment.

FIG. 9 shows tilting operations of a sound collecting part 900 of the electronic device 100 according to an example embodiment.

According to an example embodiment, the sound collecting part 900 may be configured to tilt according to the curvature of the body part of the target with which the sound collecting part 900 contacts. For example, when the user touches the electronic device 100 to the body part of the target to auscultate the target, the sound collecting part 900 may be tilted so that the surface side of the sound collecting part is in close contact with the body part of the target. Here, the sound collecting part 900 being tilted may indicate the sound collecting part 900 rotating or tilting within a certain angle.

As described above, by the sound collecting part 900 of the electronic device 100 being tilted according to the curvature of the body part of the target, the quality of obtained auscultation sound data may be improved. Specifically, when auscultating an anterior chest of a woman which is typically curvy or a target with the thin body, or when the appropriate arm angle of a user is not secured due to obstacles such as clothing, the user may more conveniently use the electronic device 100 to auscultate the target.

Figure 10A:
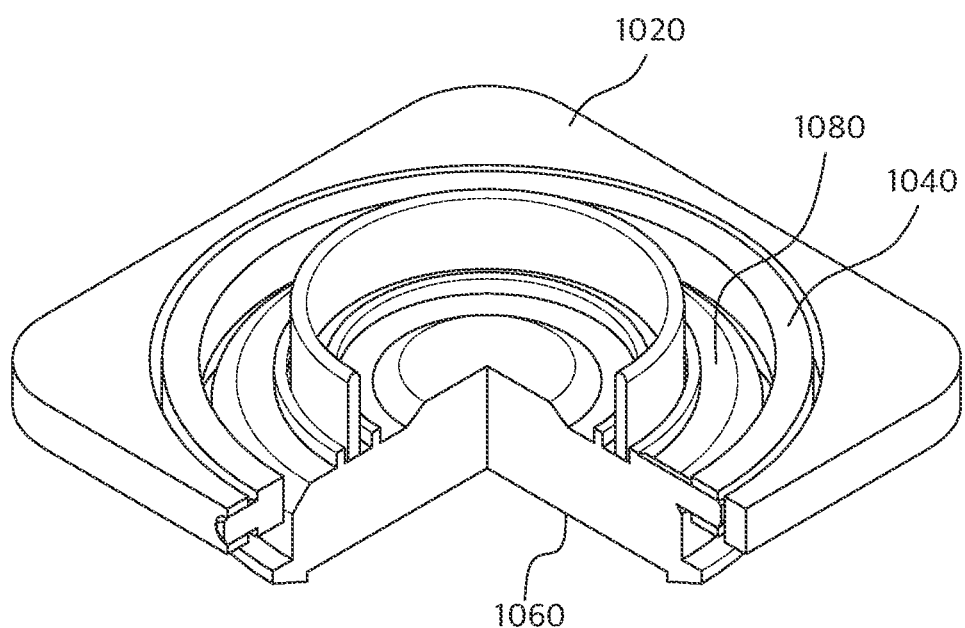
Figure 10B:
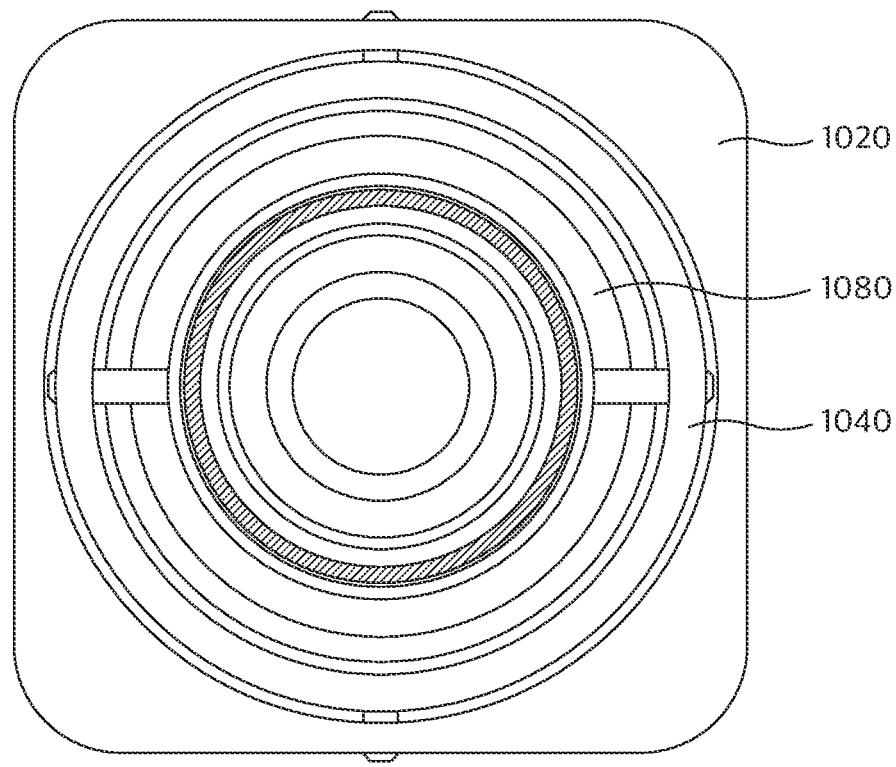
Figure 10D:
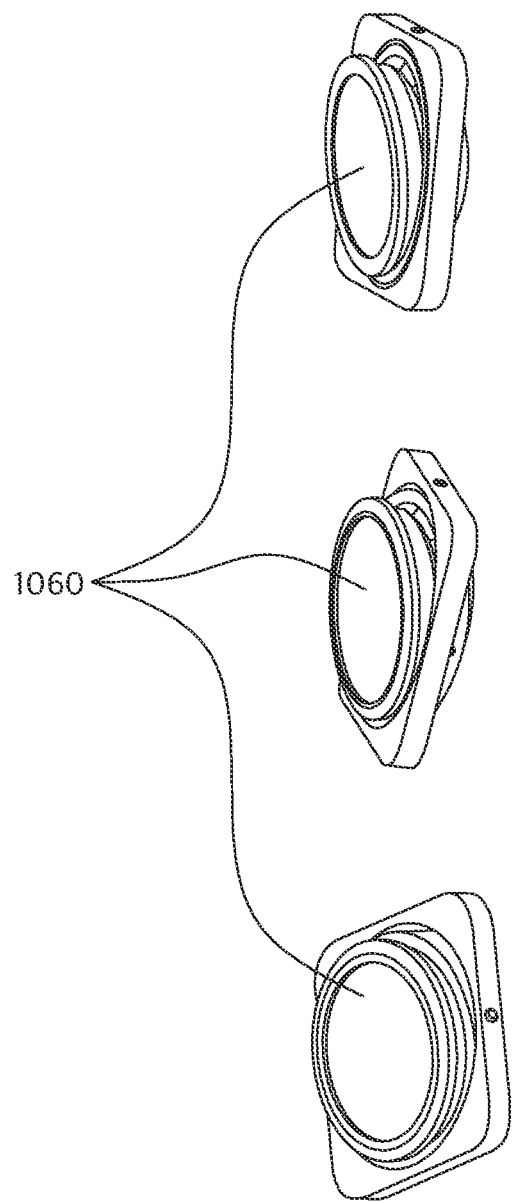

FIGS. 10A-10D illustrate an example of components of a sound collecting part 1000 of the electronic device 100 according to an example embodiment. Specifically, FIG. 10A illustrates a perspective view of the sound collecting part 1000, and FIG. 10B illustrates a rear view of the sound collecting part 1000. Further, FIGS. 10C and 10D illustrate the tiling operation of the sound collecting part 1000.

According to an example embodiment, the sound collecting part 1000 may include a first axis bracket 1020, a second axis bracket 1040, a diaphragm module 1060 and a coil spring 1080. Here, the first axis bracket 1020 may support the second axis bracket 1040 so that the second axis bracket 1040 may rotate, and the second axis bracket 1040 may support the diaphragm module 1060 so that the diaphragm module 1060 may rotate. Further, the diaphragm module 1060 may obtain vibration or sound transmitted through the skin or clothing of the target, and the coil spring 1080 is connected to the diaphragm module 1060 and may support the diaphragm module 1060 to rotate within a certain angle.

Referring to FIGS. 10A and 10B, according to an example embodiment, the first axis bracket 1020 may be connected to the housing of the electronic device 100 and serve as a base that does not rotate. Further, according to an example embodiment, the second axis bracket 1040 may be connected to the first axis bracket 1020 so that the second axis bracket 1040 may rotate in a direction perpendicular to the first axis, and according to an example embodiment, the diaphragm module 1060 may be connected to the second axis bracket 1040 so that the diaphragm module 1060 may rotate in a direction perpendicular to the second axis.

Here, the angle formed by the first axis and the second axis may be vertical as shown in FIGS. 10A and 10B, but it is only a mere example embodiment, and the angle is not limited thereto.

Referring to FIGS. 10C and 10D, in order for the diaphragm module 1060 to come into close contact with the body part of the target as the electronic device 100 moves, the second axis bracket 1040 and the diaphragm module

1060 may rotate. For example, in order for the diaphragm module 1060 to come into close contact with the body part of the target as the electronic device 100 moves, the second axis bracket 1040 may rotate in a direction perpendicular to the first axis, and the diaphragm module 1060 may rotate in a direction perpendicular to the second axis.

As described above, as the second axis bracket 1040 and the diaphragm module 1060 rotate in order for the diaphragm module 1060 of the electronic device 100 to be in close contact with the body part of the target, the quality of obtained auscultation sound data may be improved.

FIG. 11 shows a flowchart of a method of operating an electronic device according to an example embodiment.

In operation S1100, the electronic device may input first auscultation sound data obtained through a sound collecting part into a first AI model to obtain an abnormality analysis result corresponding to the first auscultation sound data.

According to an example embodiment, for each set section of the first auscultation sound data, the abnormality analysis result may include information about the probability that the auscultation sound corresponding to each set section is an abnormal sound. For example, the first auscultation sound data may include heart sound data, and information about the probability that the auscultation sound is an abnormal sound may include information about the probability that an auscultation sound is a normal sound and information about the probability that an auscultation sound is a heart murmur. Alternatively, the first auscultation sound data may include lung sound data, and information about the probability that an auscultation sound is an abnormal sound may include information about the probability that the auscultation sound is a normal sound, information about the probability that the auscultation sound is crackle, and information about the probability that the auscultation sound is wheeze.

According to an example embodiment, the abnormality analysis result may include information about the probability that the auscultation sound corresponding to the entire section of the first auscultation sound data is an abnormal sound.

According to an example embodiment, the abnormality analysis result may include at least one piece of disease information corresponding to the first auscultation sound data.

According to an example embodiment, the electronic device may obtain a first user input to obtain auscultation sound data through an input part, obtain second auscultation sound data through the sound collecting part, and output the second auscultation sound data through an audio output part. Further, the electronic device may obtain a second user input to analyze the auscultation sound data through the input part, obtain the first auscultation sound data for a set period of time from the time the second user input is obtained through the second collecting part, and input the obtained first auscultation sound data into the first AI model.

According to an example embodiment, the electronic device may input the first auscultation sound data into a second AI model and remove noise included in the first auscultation sound data, and the electronic device may obtain an abnormality analysis result by inputting the first auscultation sound data from which noise is removed into the first AI model.

According to an example embodiment, the electronic device may obtain auscultation position data through the input part, and may input the first auscultation sound data and the auscultation position data into the first AI model to obtain an abnormality analysis result corresponding to the first auscultation sound data. For example, the electronic device may provide one or more auscultable positions through a display, and the electronic device may obtain a user input for selecting at least one auscultable position among the one or more auscultable positions through the input part.

According to an example embodiment, the electronic device may obtain biometric data about the auscultation target through an image sensor, and input the first auscultation sound data and the biometric data into the first AI model to obtain an abnormality analysis result corresponding to the first auscultation sound data.

According to an example embodiment, the electronic device may obtain body temperature data about an auscultation target through a temperature sensor, and the electronic device may input the first auscultation sound data and the body temperature data into the first AI model to obtain an abnormality analysis result corresponding to the first auscultation sound data.

In operation S1150, the electronic device may provide the abnormality analysis result through the display.

According to an example embodiment, through the display, the electronic device may provide information about a section where the probability that the auscultation sound is an abnormal sound is greater than or equal to a set value, among set sections of the first auscultation sound data.

According to an example embodiment, the electronic device may provide a graph corresponding to the second auscultation sound data through the display.

According to an example embodiment, the first auscultation sound data may include heart sound data, and by inputting the heart sound data into a third AI model, the electronic device may obtain at least one of information about heart beat regularity corresponding to the heart sound data and information about heart rate, and the electronic device may provide at least one of the information about heart beat regularity and the information about heart rate.

According to an example embodiment, the first auscultation sound data may include lung sound data, and the electronic device may input the lung sound data into a fourth AI model to obtain at last one of information about respiratory regularity and information about respiratory rate corresponding to the lung sound data, and the electronic device may provide at least one of the information about respiratory regularity and the information about respiratory rate through the display.

FIG. 12 shows a block diagram of the electronic device 100 according to an example embodiment.

According to an example embodiment, the electronic device 100 may include a handle 1200, a display 1220, a sound collecting part 1240 and a controller 1260. In FIG. 12 illustrating the electronic device 100, only components related to the example embodiment are illustrated. Therefore, it is apparent to those skilled in the art that the electronic device 100 may further include other general-purpose components in addition to the components illustrated in FIG. 12. Among the descriptions above regarding the electronic device 100, the overlapping contents will be briefly explained or omitted.

The handle 1200 is an element for holding the electronic device 100 when a user uses it, and the handle 1200 may be formed on one part of housing of the electronic device 100.

As an element for providing various visual information to a user, the display 1220 may be positioned on another part of the housing and may be placed on one surface side of the housing.

The sound collecting part 1240 is an element for obtaining biological signals of a target, and the sound collecting part 1240 may be positioned on the other part of the housing and may be placed on another surface side of the housing.

The controller 1260 may control the overall operation of the electronic device 100 and process data and signals. The controller 1260 may be composed of at least one hardware unit. Further, the controller 1260 may operate by one or more software modules generated by executing program codes stored in a memory. The controller 1260 may include a processor and a memory, and the processor may control the overall operation of the electronic device 100 and process data and signals by executing program codes stored in the memory. Further, in an example embodiment, the controller 1260 may include at least one processor.

The controller 1260 may be configured to input the first auscultation sound data obtained through the sound collecting part into the first AI model to obtain an abnormality analysis result corresponding to the first auscultation sound data, and provide the abnormality analysis result through the display.

The electronic device according to the above-described example embodiments may include a processor, a memory for storing and executing program data, a permanent storage such as a disk drive, and/or a user interface device such as a communication port, a touch panel, a key and/or a button that communicates with an external device. Methods implemented as software modules or algorithms may be stored in a computer-readable recording medium as computer-readable codes or program instructions executable on the processor. Here, the computer-readable recording medium includes a magnetic storage medium (for example, ROMs, RAMs, floppy disks and hard disks) and an optically readable medium (for example, CD-ROMs and DVDs). The computer-readable recording medium may be distributed among network-connected computer systems, so that the computer-readable codes may be stored and executed in a distributed manner. The medium may be readable by a computer, stored in a memory, and executed on a processor.

The example embodiments may be represented by functional block elements and various processing steps. The functional blocks may be implemented in any number of hardware and/or software configurations that perform specific functions. For example, an example embodiment may adopt integrated circuit configurations, such as memory, processing, logic and/or look-up table, that may execute various functions by the control of one or more microprocessors or other control devices. Similar to that elements may be implemented as software programming or software elements, the example embodiments may be implemented in a programming or scripting language such as C, C++, Java, assembler, etc., including various algorithms implemented as a combination of data structures, processes, routines, or other programming constructs. Functional aspects may be implemented in an algorithm running on one or more processors. Further, the example embodiments may adopt the existing art for electronic environment setting, signal processing, and/or data processing. Terms such as "mechanism," "element," "means" and "configuration" may be used broadly and are not limited to mechanical and physical elements. The terms may include the meaning of a series of routines of software in association with a processor or the like.

Closings Statement

The above-described example embodiments are merely examples, and other embodiments may be implemented within the scope of the claims. It will be understood that many additional changes in the details, materials, steps and arrangement of parts, which have been herein described and illustrated to explain the nature of the subject matter, may be made by those skilled in the art within the principle and scope of the invention as expressed in the appended claims.

What is claimed is:

1. An electronic device comprising:
   a housing with a handle that is formed on one part of the housing;
   a display that is positioned on another part of the housing and placed on one surface side of the housing;
   a sound collecting part that is positioned on the other part of the housing and placed on another surface side of the housing, wherein the sound collecting part comprises:
      a first axis bracket connected to the housing of the electronic device and serving as a base that does not rotate;
      a second axis bracket that is connected to the first axis bracket and rotates in a vertical direction perpendicular to a first axis; and
      a diaphragm module that is connected to the second axis bracket and rotates in a vertical direction perpendicular to a second axis,
      wherein the second axis bracket and the diaphragm module rotate in order for a diaphragm to come into close contact with a body part as the electronic device moves; and
   a controller,
   wherein the electronic device:
      inputs first auscultation sound data obtained through the sound collecting part into a first artificial intelligence (AI) model and obtains an abnormality analysis result corresponding to the first auscultation sound data; and
      provides the abnormality analysis result through the display,
   wherein the first artificial intelligence (AI) model is a one dimensional convolutional neural network model.

2. The electronic device of claim 1, wherein, for each set section of the first auscultation sound data, the abnormality analysis result includes information about probability that auscultation sound corresponding to the each set section is an abnormal sound.

3. The electronic device of claim 2,
   wherein the first auscultation sound data includes heart sound data,
   and wherein the information about probability that the auscultation sound is an abnormal sound includes information about probability that the auscultation sound is a normal sound and information about probability that the auscultation sound is heart murmur.

4. The electronic device of claim 2,
   wherein the first auscultation sound data includes lung sound data,
   and wherein the information about probability that the auscultation sound is an abnormal sound includes information about probability that the auscultation sound is a normal sound, information about probability that the auscultation sound is a crackle, and information about probability that the auscultation sound is a wheeze.

5. The electronic device of claim 4, wherein the abnormality analysis result includes at least one piece of lung disease information corresponding to the first auscultation sound data.

6. The electronic device of claim 2, wherein the controller provides information about a section where the probability that the auscultation sound is an abnormal sound is greater than or equal to a set value, among set sections of the first auscultation sound data through the display.

7. The electronic device of claim 1, wherein the abnormality analysis result includes information about probability that auscultation sound is an abnormal sound corresponding to an entire section of the first auscultation sound data.

8. The electronic device of claim 1, further comprising:
an audio output part; and
an input part to obtain a user input,
wherein the controller is configured to:
obtain a first user input to obtain auscultation sound data through the input part;
obtain second auscultation sound data through the sound collecting part;
output the second auscultation sound data through the audio output part;
obtain a second user input to analyze auscultation sound data through the input part;
obtain the first auscultation sound data for a set period of time from a time point that the second user input is obtained through the sound collecting part; and
input the obtained first auscultation sound data into the first AI model.

9. The electronic device of claim 8, wherein the controller is configured to provide a graph corresponding to the second auscultation sound data through the display.

10. The electronic device of claim 1, wherein the controller is configured to input the first auscultation sound data into a second AI model to remove noise included in the first auscultation sound data, and input the first auscultation sound data from which the noise is removed into the first AI model to obtain the abnormality analysis result.

11. The electronic device of claim 1,
wherein the first auscultation sound data includes heart sound data,
and wherein the controller is configured to:
input the heart sound data into a third AI model to obtain at least one of information about heart beat regularity corresponding to the heart sound data and information about heart rate corresponding to the heart sound data; and
provide at least one of the information about heart beat regularity and the information about heart rate through the display.

12. The electronic device of claim 1,
wherein the first auscultation sound data includes lung sound data,
and wherein the controller:
inputs the lung sound data into an additional AI model to obtain at least one of information about respiratory regularity corresponding to the lung sound data and information about respiratory rate corresponding to the lung sound data; and
provides at least one of the information about respiratory regularity and the information about respiratory rate through the display,
wherein the additional artificial intelligence (AI) model is a one dimensional convolutional neural network model.

13. The electronic device of claim 1, further comprising an input part for obtaining a user input,
and wherein the controller:
obtains auscultation position data through the input part; and
inputs the first auscultation sound data and the auscultation position data into the first AI model to obtain the abnormality analysis result corresponding to the first auscultation sound data.

14. The electronic device of claim 13, wherein the controller, to obtain the auscultation position data,
provides one or more auscultable positions through the display; and
obtains a user input for selecting at least one auscultable position among the one or more auscultable positions through the input part.

15. The electronic device of claim 1, further comprising an image sensor,
wherein the controller is configured to:
obtain biometric data about an auscultation target through the image sensor; and
input the first auscultation sound data and the biometric data into the first AI model to obtain the abnormality analysis result corresponding to the first auscultation sound data.

16. The electronic device of claim 1, further comprising a temperature sensor,
wherein the controller is configured to:
obtain body temperature data of the auscultation target through the temperature sensor; and
input the first auscultation sound data and the body temperature data into the first AI model to obtain the abnormality analysis result corresponding to the first auscultation sound data.

17. The electronic device of claim 1, wherein the sound collecting part is configured to be tilted according to curvature of the body part with which the sound collecting part contacts.

* * * * *